(12) United States Patent
Vacca

(10) Patent No.: US 7,419,469 B2
(45) Date of Patent: Sep. 2, 2008

(54) METHOD AND SYSTEM FOR DIAGNOSTIGRAPHIC BASED INTERACTIONS IN DIAGNOSTIC MEDICAL IMAGING

(75) Inventor: Paul P. Vacca, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 764 days.

(21) Appl. No.: 10/875,875

(22) Filed: Jun. 24, 2004

(65) Prior Publication Data

US 2005/0289173 A1 Dec. 29, 2005

(51) Int. Cl.
*A61B 8/00* (2006.01)
*G06F 3/00* (2006.01)

(52) U.S. Cl. ...................... 600/437; 715/700
(58) Field of Classification Search .......... 600/407, 600/409, 437, 443, 447; 702/19, 39, 127, 702/137; 707/102; 710/5, 11; 715/700, 715/703; 717/112

See application file for complete search history.

(56) References Cited

U.S. PATENT DOCUMENTS

| | | | | |
|---|---|---|---|---|
| 4,739,318 | A | * 4/1988 | Cohen | 345/472.3 |
| 5,544,654 | A | 8/1996 | Murphy et al. | 128/660.07 |
| 5,742,779 | A | 4/1998 | Steele et al. | 345/349 |
| 6,038,538 | A | 3/2000 | Agrawal et al. | 705/7 |
| 6,195,101 | B1 | 2/2001 | Ghislain Bossut et al. | 345/433 |
| 6,442,512 | B1 | 8/2002 | Sengupta et al. | 703/6 |
| 6,458,081 | B1 * | 10/2002 | Matsui et al. | 600/437 |
| 6,507,845 | B1 | 1/2003 | Cohen et al. | 707/100 |
| 6,514,201 | B1 | 2/2003 | Greenberg | 600/437 |
| 6,539,404 | B1 | 3/2003 | Ouchi | 707/500 |
| 6,567,783 | B1 | 5/2003 | Notani et al. | 705/9 |

FOREIGN PATENT DOCUMENTS

| | | |
|---|---|---|
| JP | 10074113 | 3/1998 |
| JP | 2000226498 | 7/2000 |
| WO | WO 01/96906 A1 | 12/2001 |

OTHER PUBLICATIONS eScription—IntelliScript Dictation Server Work Flow Diagram, obtained May 7, 2004 at internet address http://www.escription.com/intelliscript_workflow.htm, 1 page.

(Continued)

*Primary Examiner*—Francis J. Jaworski

(57) ABSTRACT

An ideographical language framework is disclosed that is designed to enable the description and communication of a series of workflow steps. An ideogram is defined as a character or symbol representing an idea or thing without expressing the pronunciation of a particular word or words for it, i.e. not dependent on any specific natural language representation. Further, an ideogram may further be culturally independent as well. A workflow is defined as the activities, e.g. tasks or procedural steps, entities involved, i.e. participants, such as people, organizations, machines, etc., inputs and outputs, states, requisite tools, and the relationships therebetween, for each step in a process. The various activities, entities, inputs, outputs, tools and relationships are referred to as workflow elements. The disclosed embodiments represent workflow elements of a given workflow using ideograms meaningful to workflow participants, i.e. entities, and composed according to a syntax that enables easy recognition and use of a set of workflow instructions.

70 Claims, 38 Drawing Sheets

OTHER PUBLICATIONS

Learnalanguage—Project organization workflow example, obtained May 7, 2004 at internet address http://www.learnalanguage.org/caac/ 2 pp.

ManageStar—advertising, obtained May 7, 2004 at internet address http://www.managestar.com/ 1 page.

Andrew Begel, publication, "LogoBlocks: A Graphical Programming Language for Interacting with the World," May 24, 1996, 23 pp.

David Spencer Lees, Dissertation, "A Graphical Programming Language for Service Robots in Semi-Structured Environments," Feb. 1994, 164 pages.

* cited by examiner

FIG. 3
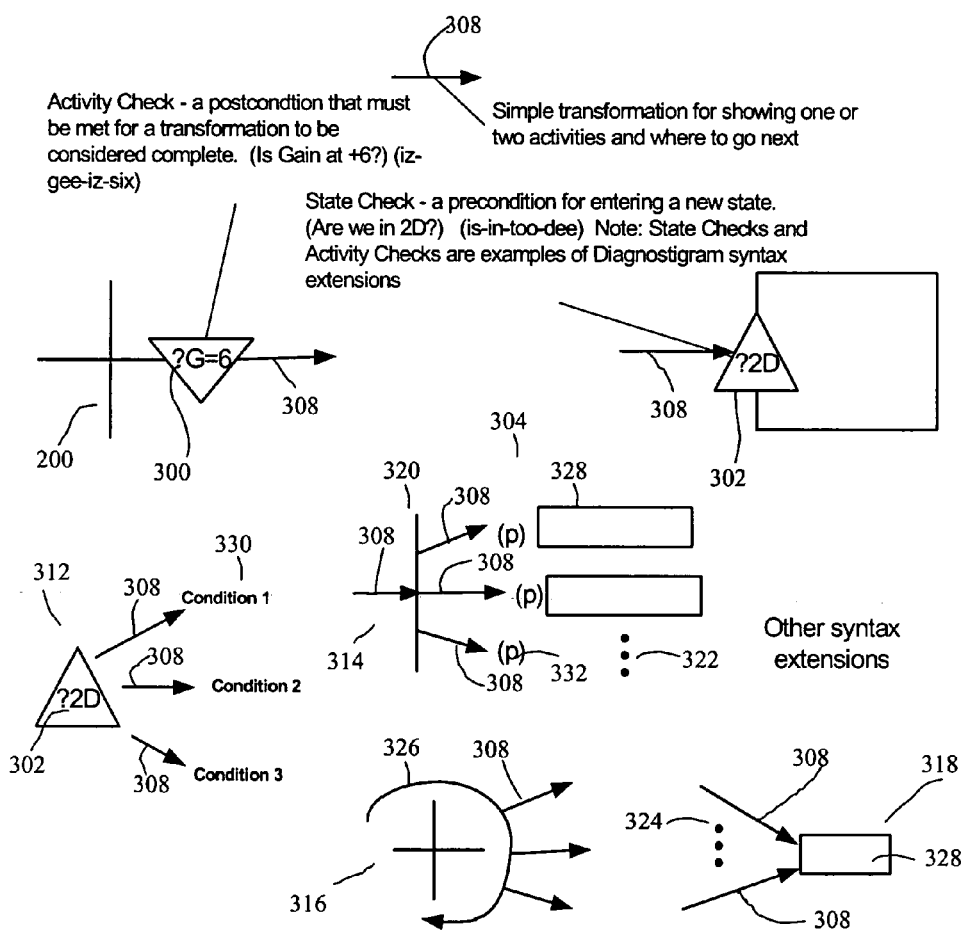
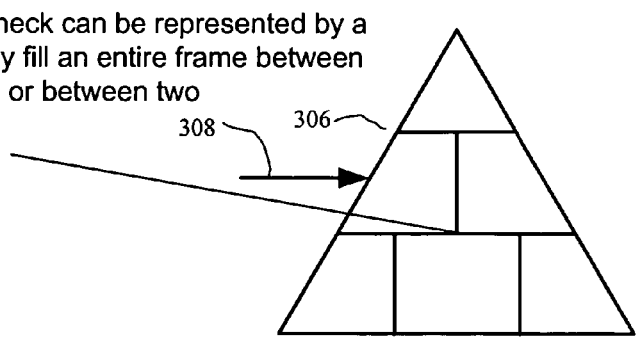
Complex Activity or State Check can be represented by a subdivided triangles and may fill an entire frame between a transformation and a state or between two transformations.

Target Frame

FIG. 7
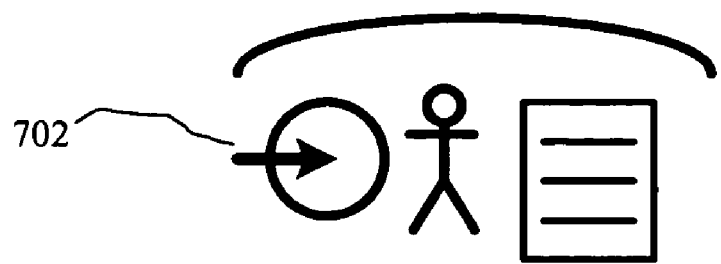
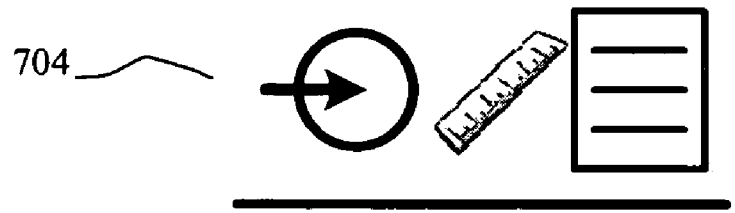

FIG. 10A

| ID | Type | Type | Diagnostigram | Glyph | Description | Literal Phoneme | Ideographic Phoneme |
|---|---|---|---|---|---|---|---|
| 1 | Gen | Cmd | | ↑ | Start, Turn on, Enter, Use | Start | on |
| 2 | Gen | Cmd | | | End, Turn off, Finish Enter Color M Mode | End | end |
| 3 | Gen | Cmd | | | Start New | Start | on |
| 4 | Gen | Cmd | | | List  List Old Exams | List | lis |
| 5 | Gen | Cmd | Picture: Human hand | | Use, do  USE (PROC IN) 6L3 TRANSDUCER  UNPLUG 6L3 TRANSDUCER | Use, do | do |
| 6 | Gen | Cmd | | | Select, Setup, Set, Insert | Select | sel |
| 7 | Gen | Cmd | | | Deselect, Unset, Remove | Deselect | desel |
| 8 | Gen | Cmd | | | Delete | Delete | del |
| 9 | Gen | Cmd | | | Enter | Enter | ent |
| 10 | Gen | Cmd | | | Exit | Exit | ex |

FIG. 10B

| ID | Type | Type | Diagnostigram | Glyph | Description | Literal Phoneme | Ideographic Phoneme |
|---|---|---|---|---|---|---|---|
| 11 | Gen | Cmd | | | Choose, choices on branches may be three parallel workflows or they may merge back to one or two; choices may be marked with Diagnostigram ? or choices may lead to termination Diagnostigram. | | |
| 12 | Gen | Cmd | | | Repeat the enclosed Diagnostigrams | Repeat | repee |
| 13 | Gen | Cmd | Two brackets | | Redo | Redo | redo |
| 14 | Gen | Cmd | Picture: Sound coming out of a speaker | | Play audio | Play audio | Play |
| 15 | Gen | Cmd | Redo and Play | | Replay | Replay | reeplay |
| 16 | Gen | Cmd | Picture: Open eye | | Display | Display | sho |
| 17 | Gen | Cmd | Redo and display | | Redisplay | Re display | reesho |

FIG. 10C

| ID | Type | Type | Diagnostigram | Glyph | Description | Literal Phoneme | Ideographic Phoneme |
|----|------|------|---------------|-------|-------------|-----------------|---------------------|
| 18 | Cmd | US | Picture: Sequoia Tree, Sequioa logo | | Optimize, optimize image, optimize and analyze image in specified mode or view<br><br>OPTIMIZE 2D IMAGE | Optimize | ize |
| 19 | Gen | Cmd | Picture: Dancer performing | | Perform<br><br>PERFORM CARDIAC STUDY | Perform | perf |
| 20 | Gem | Cmd | Picture: Page with lines of text | | Report Data | Report | rep |

FIG. 10D

| ID | Type | Type | Diagnostigram | Glyph | Description | Literal Phoneme | Ideographic Phoneme |
|---|---|---|---|---|---|---|---|
| 21 | Gem | Cmd | Picture: Page with text entry boxes | 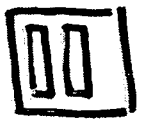 | Form, Input Data | Input | inp |
| 22 | Gen | Object Cmd | Picture: Printer with a sheet of paper coming out the top 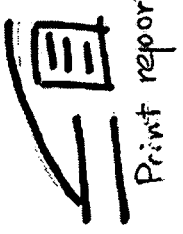 |  | Printer, Print, save to local printer  Print report 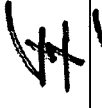 Print Demographic Report | Print | prin |
| 23 | Gen, US | Object Cmd | |  | DICOM Printer, save to network disk, save to DICOM storage | DICOM print | diprin |
| 24 | Gen, US | Object Cmd | | | Black and White Printer, print to local black & white printer | Black White print | beeprin |

FIG. 10E

| ID | Type | Type | Diagnostigram | Glyph | Description | Literal Phoneme | Ideographic Phoneme |
|---|---|---|---|---|---|---|---|
| 25 | Gen, US | Object Cmd | | | Color Printer, print to color printer | Color print | koprin |
| 26 | Gen, US | Object Cmd | | | Color DICOM Printer, save to color DICOM printer | DICOM Color print | kodiprin |
| 27 | Gen | Object | Picture: Computer workstation | | System | System | Sys |
| | | | | | Turn System On, Turn System Off, Power Off | Turn on, Turn off, Power off | on off powoff |

FIG. 10F

| ID | Type | Type | Diagnostigram | Glyph | Description | Literal Phoneme | Ideographic Phoneme |
|----|------|------|---------------|-------|-------------|-----------------|---------------------|
| 28 | Gen | Cmd | Picture: Computer monitor |  | Display, Screen, Monitor  PRINT SCREEN | Display Screen | disp scrin |
| 29 | Gen | Object Cmd | Picture: Floppy disk |  | Disk, Save to disk  LOAD IMAGE FROM DISK | Save | sav |
| 30 | Gen | Object Cmd | Picture: Floppy disk with lightning | 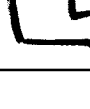 | DICOM Storage, Save to DICOM storage | Network Save | netsav |

| ID | Type | Type | Diagnostigram | Glyph | Description | Literal Phoneme | Ideographic Phoneme |
|---|---|---|---|---|---|---|---|
| 31 | US | Object | Picture: Ultrasound transducer |  | Transducer, use transducer | Transducer or x-ducer | doos |

FIG. 10H

| ID | Type | Type | Diagnostigram | Glyph | Description | Literal Phoneme | Ideographic Phoneme |
|---|---|---|---|---|---|---|---|
| 32 | US | Object Cmd | Picture: Handheld Camera | | Image, capture image SAVE IMAGE TO DISK | Image | Pic<br><br>picsav<br><br>Picnet or picnetsav |
| 33 | US | Object Cmd | Picture: TV Camera | | Cine, start Cine START CINE | Cine | sin |
| 34 | US | Object Cmd | Picture: Movie camera | | Clip, save clip Set Clip Range 12..36 out of 55 frames captured L 12 R 36 55<br>Send Clip to Dicom Storage | Clip | Clip<br><br>netclip |
| 35 | Gen | Object | Picture: VCR deck | | VCR, could also be save to VCR (same as start recording) or VCR play, depending on context | VCR save | vid |
| 36 | Gen | Cmd | | | VCR play | VCR play | vplay |
| 37 | Gen | Cmd | | | VCR start recording | VCR record | vec |
| 38 | Gen | Cmd | | | VCR pause | VCR pause | vas |
| 39 | Gen | Cmd | | | VCR fast forward | VCR forward | forward |

FIG. 10I

| ID | Type | Type | Diagnostigram | Glyph | Description | Literal Phoneme | Ideographic Phoneme |
|---|---|---|---|---|---|---|---|
| 40 | Gen | Cmd | | | VCR rewind | VCR rewind | rewind |
| 41 | Gen | Cmd | | | VCR end | VCR forward | vend |
| 42 | Gen | Cmd | | | VCR beginning | VCR front | vont |
| 43 | Gen | Cmd | | | VCR stop | VCR stop | vop |
| 44 | Gen | Cmd | | | VCR power off or VCR Stop | VCR off | voff |
| 45 | Gen | Object | Picture: Person | or | Person, demographic enter demographic data. | Person | pers |
| 46 | Gen | Object | Picture: Man | | Man, Male | Man | man |
| 47 | Gen | Object | Picture: Woman | | Woman, Female Pregnant woman | Woman | wo |
| 48 | Gen | Object | Picture: Child | | Child, Adolescent | Child | kid |

FIG. 10J

| ID | Type | Type | Diagnostigram | Glyph | Description | Literal Phoneme | Ideographic Phoneme |
|---|---|---|---|---|---|---|---|
| 49 | Gen | Object | Picture: | ᨒ Infant Boy | Baby, Infant | Baby | babe |
| 50 | Gen | Object Anatomy | Picture: Kidney | ⬭ | Kidney | Kidney | kid |
| 51 | Gen | Object Anatomy | Picture: Liver | ⬯ | Liver | Liver | liv |
| 52 | Gen | Object Anatomy | Picture: Head | ⌒ | Head, Cranial | Head | Hed |
| 53 | Gen | Object | Picture: Heart | ♡ | Heart, Cardio | Heart | har |
| 54 | Gen | Object | | < > | Exam Type, Study Type, Protocol Category ⟨⟩ ⟨PLAX⟩ perform produced long axis view  setup for echocard study  ⟨⟩ print report of an infant cranial study | Exam Type | extyp |

FIG. 10K

| ID | Type | Type | Diagnostigram | Glyph | Description | Literal Phoneme | Ideographic Phoneme |
|---|---|---|---|---|---|---|---|
| 55 | Gen | Object | |《 》 | Preset, Exam Preset, Image Preset : collection of pre-set parameters for specific exam, study or protocol type <br><br> use stress echo preset | Preset | preset |
| 56 | Gen, US | Attr | Echo and a person | | Ultrasound | Ultrasound | us |
| 57 | Gen, US | Attr | Magnet and a person | | MRI, Magnetic Resonance Imaging | MRI | mir |
| 58 | US | Object Mode | 2 D Diagnostic Screen | | 2D or Bmode Imaging Mode <br><br> Enter 2D | Two D | toodee |
| 59 | US | Object Mode | 3D Diagnostic Screen | | 3D <br><br> BEGIN 3D | Three D | teedee |

FIG. 10L

| ID | Type | Type | Diagnostigram | Glyph | Description | Literal Phoneme | Ideographic Phoneme |
|---|---|---|---|---|---|---|---|
| 60 | US | Object Mode | Colored box | [hatched box glyph] | Color Doppler Mode<br>[sketch] Enter Color Doppler | CD | kolo |
| 61 | US | Object Mode | Motion, a cursor and an M | ≡\|M | M-Mode, Motion Mode<br>[sketch] ≡\|M Enter M-Mode | M-Mode | emo |
| 62 | US | Object | Wave and PW | ∿PW | Pulse Width Doppler Mode<br>[sketch] ∿PW Enter PW | PW | pew |
| 63 | US | Object | Wave and CW | ∿CW | Continuous Wave Doppler Mode<br>[sketch] ∿CW Enter CW | CW | kew |

FIG. 10M

| ID | Type | Type | Diagnostigram | Glyph | Description | Literal Phoneme | Ideographic Phoneme |
|---|---|---|---|---|---|---|---|
| 64 | US | Cmd, Mode | Picture: ruler or calculator | | Calc, Enter Calc | Calc | calc |
| 65 | US | Object | Picture: hammer | | Utility, utilities Enter Study Utilities | Utilities, Utility or Util | ute |
| 66 | US | Object | Picture: caliper | | Caliper, take measurement | Measure | mez |
| 67 | US | Cmd Func | | | Res, Rescan selected area and resolve up to full screen | Res | Res |
| 68 | US | Cmd Func | | | Zoom Up | Zoom Up | zomup |
| 69 | US | Cmd Func | | | Zoom Down | Zoom Down | zomdon |

FIG. 10N

| ID | Type | Type | Diagnostigram | Glyph | Description | Literal Phoneme | Ideographic Phoneme |
|---|---|---|---|---|---|---|---|
| 70 | US | Cmd Func | | ?!! or ~ | TEQ Tissue Equalization | T.E.Q | teek |
| 71 | US | Param | | ↓↓↓↓ | DGC | DGC | deegee |
| 72 | US | Param | | ✓+++ | Gain | Gain | gane |
| 73 | US | Param | | )+++ | Depth | Depth | dep |
| 74 | US | Param | | )○+++ | Brightness | Brightness | brite |
| 75 | US | Param | | I+++ | Dynamic Range | Dynamic Range | dyna |
| 76 | US | Param | | ⊙+++ | Focus | Focus | foc |

FIG. 10O

| ID | Type | Type | Diagnostigram | Glyph | Description | Literal Phoneme | Ideographic Phoneme |
|----|------|------|---------------|-------|-------------|-----------------|---------------------|
| 77 | US | Param | |  | Multi-Hz (frequency) | Multi Hertz | freek |
| 78 | US | Param | | 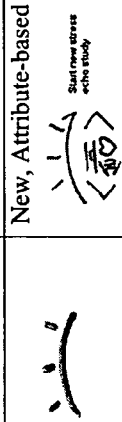 | Contrast | Contrast | cont |
| 79 | Gen | Attr | Picture: X the algebraic unknown | ✗ | Number, plural | | |
| 80 | Gen | Attr | Picture: sunrise | 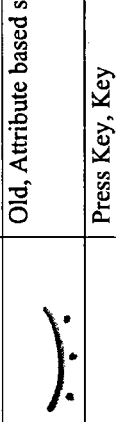 | New, Attribute-based spanning connector | | |
| 81 | Gen | Attr | Picture: chin with a beard | 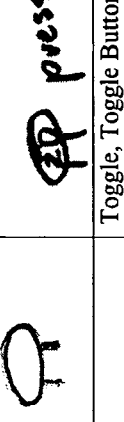 | Old, Attribute based spanning connector | | |
| 82 | Cmd | Low Level Cmd | Picture: typewriter key | ⌒ | Press Key, Key | Key | key |
| 83 | Cmd | Low | Picture: Switch | ⌒ | Toggle, Toggle Button 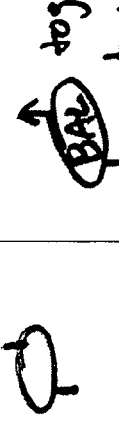 | Toggle | tog |

FIG. 10P

| ID | Type | Type | Diagnostigram | Glyph | Description | Literal Phoneme | Ideographic Phoneme |
|---|---|---|---|---|---|---|---|
| 84 | Syntax | Meta | Picture: Stethoscope and D-shaped ear | 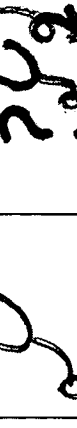 | Diagnostigram, workflow element or diagnosis  un less please provide more detail 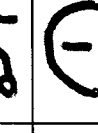 reply diagnostigram transmitted into spoken language | Diagnostig ram | dagm |
| 85 | Syntax | Meta | Picture: Stethoscope and Graph |  | Diagnostigraph, workflow | Diagraph | daf |
| 86 | Syntax | Cmd | |  | Status Check, perform status check | Status | Stat or bang |
| 87 | Cmd | US | | 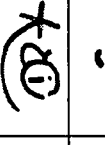 | Review or Start Review | Review | rev |
| 88 | Cmd | US | |  | Start Review, Enter Review | Start Review | Rev or gorev |
| 89 | Cmd | US | |  | Stop Review, Exit Review | Exit Review | exrev |
| 90 | Cmd | US | |  | Edge | Edge | edg |

FIG. 10Q

| ID | Type | Type | Diagnostigram | Glyph | Description | Literal Phoneme | Ideographic Phoneme |
|----|------|------|---------------|-------|-------------|-----------------|---------------------|
| 91 | Cmd | US | | — | Post | Post | post |
| 92 | Cmd | US | | | Physio | Physio | fiz |
| 93 | Cmd | US | | | Image Width | Image width | wid |
| 94 | Cmd | Gen | Picture: Stopwatch or pocket watch | | Start or restart timer | Start timer | gotim |
| 95 | | | | | Stop Timer | Stop timer | extim |
| 96 | | | | | Pause Timer | Pause timer | patim |
| 97 | | | | | Set Duration | Set timer 5 minutes | Setim 5 |

FIG. 10R

| ID | Type | Type | Diagnostigram | Glyph | Description | Literal Phoneme | Ideographic Phoneme |
|---|---|---|---|---|---|---|---|
| 98 | Cmd | Gen | Picture: Hypodermic needle | | Inject | Inject | Jek |
| | | | | | INJECT STRESS AGENT | Inject Stress Agent | jekess |
| | | | | | INJECT CONTRAST AGENT | Inject Contrast Agent | jekast |
| 99 | Cmd | US | Picture: Icicles | | Freeze | Freeze | freez |
| 100 | Cmd | US | | | Unfreeze | Unfreeze | xfreez |
| 101 | Cmd | US | Picture: Man running | | Run (a synonym for unfreeze) | Run | run |

FIG. 10S

| ID | Type | Type | Diagnostigram | Glyph | Description | Literal Phoneme | Ideographic Phoneme |
|---|---|---|---|---|---|---|---|
| 102 | Cmd | US | Picture: horizontal mirror image of a small a *(UP DOWN INVERT)* | *(glyph)* | Invert, Up Down Invert. Command that flips the image display upside down or back *(Flip Vector Transducer Image Upside Down)* | Up down Invert | invert |
| 103 | Cmd | US | Picture: vertical mirror image of a small a *(LEFT RIGHT INVERT)* | *(glyph)* | Left Right Invert. Command that flips the image display side to side or back *(Flip Vector Transducer Image Side to Side)* | Left Right Invert | livert |
| 104 | Syntax | Layout | | ( | Semantic span connectors; placed over or under a set of Diagnostigrams to indicate an associative meaning. Some Diagnostigrams have their own span connectors as part of their glyph. See Start, Print, New, etc. | | |
| 105 | Syntax | Struct | | = | Implementation span connectors; placed over or under a set of low level commands and objects to indicate they are activated together | | |

FIG. 10T

| ID | Type | Type | Diagnostigram | Glyph | Description | Literal Phoneme | Ideographic Phoneme |
|---|---|---|---|---|---|---|---|
| 106 | Syntax | Layout | | See next line | Panel Diagnostigraph frames are organized within Panels, in a visual flow that makes sense to the reader but may be constrained so that temporal flow can be depicted as orthogonal to structural decomposition. Panel outlines need not be visible.<br>Frame Container of Diagnostigrams, containing acts and objectives, organized in a visual flow that makes sense to the reader. Frames need not be visible and may utilize internal structural aids such as grids | Panel<br><br>Frame | Pan<br><br>fram |
| | | | | 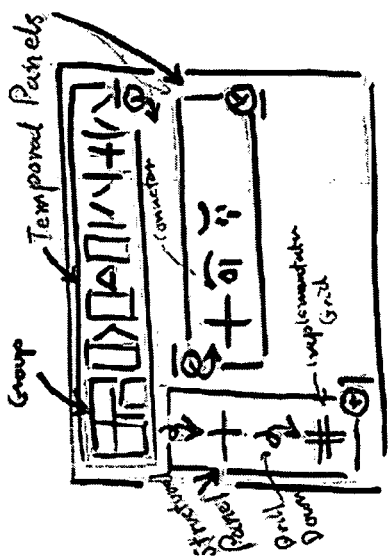 | | | |
| 107 | Syntax | Layout | | + | Activity Grid, Indicator Grouping, may be thought of us a 4 group semantic span connectors. Other grid configurations pssoible as makes visual sense and grid compartments may hold other grids, though generally this is accomplished by alias-replacement or drill down. | Grid | grid |

| ID | Type | Type | Diagnostigram | Glyph | Description | Literal Phoneme | Ideographic Phoneme |
|---|---|---|---|---|---|---|---|
| | Syntax | Struct | | | | | |
| 108 | | | |  | Instrumentation Grid, Low Command Grouping, may be thought of as 4 group implementation level span connectors | Low Grid | Iod |

FIG. 10V

| ID | Type | Type | Diagnostigram | Glyph | Description | Literal Phoneme | Ideographic Phoneme |
|---|---|---|---|---|---|---|---|
| 109 | Syntax | Cmd | | 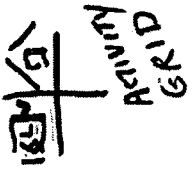 | Drill down, indicates explication, exposing lower levels to provide more detailed for the less experienced user or for the designer  | Drill | dril |
| 110 | Syntax | Cmd | | 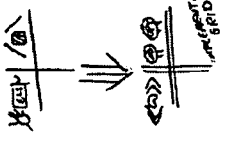 | Elaborate, indicates transition from indication to representation, implementation or instrumentation. Below this level non-Diagnostigram notations are displayed in instrumentation grids. 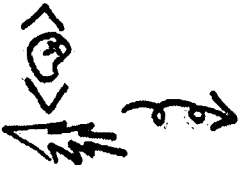 | Elaborate | elab |

Note: Continuation Diagnostigrams below are shown in reference to a Left-To-Right, temporal workflow. They are generally only needed if the Diagnostigraph contains both substantial hierarchical sentences in addition to the usual temporal workflow sentences. If layout policy is that temporal workflow is in some other direction, then these Diagnostigrams would vary appropriately.

| | | | | | |
|---|---|---|---|---|---|
| 111 | Syntax | Flow | ⊗ | End Workflow<br>Syntax flow Diagnostigrams only have meaning at panel boundaries | End Workflow | e.flo |
| 112 | Syntax | Flow | ⊗| | End Workflow, End Temporal Diagnostigraph Panel, End Horizontal Diagnostigraph when workflow and structural decomposition are present in the same Diagnostigraph | | |
| | | | ⊗| | End Structural Decomposition, End Structural Diagnostigraph Panel, End Vertical Diagnostigraph | End Structure | e.struct |
| 113 | Syntax | Flow | ↷ | Continued at next horizontal panel | At Next Horizontal | hex |
| 114 | Syntax | Flow | ↶ | Continued from prior horizontal panel | From Next Horizontal | fex |

FIG. 10W

High Level Mode-Oriented Workflow

FIG. 11C
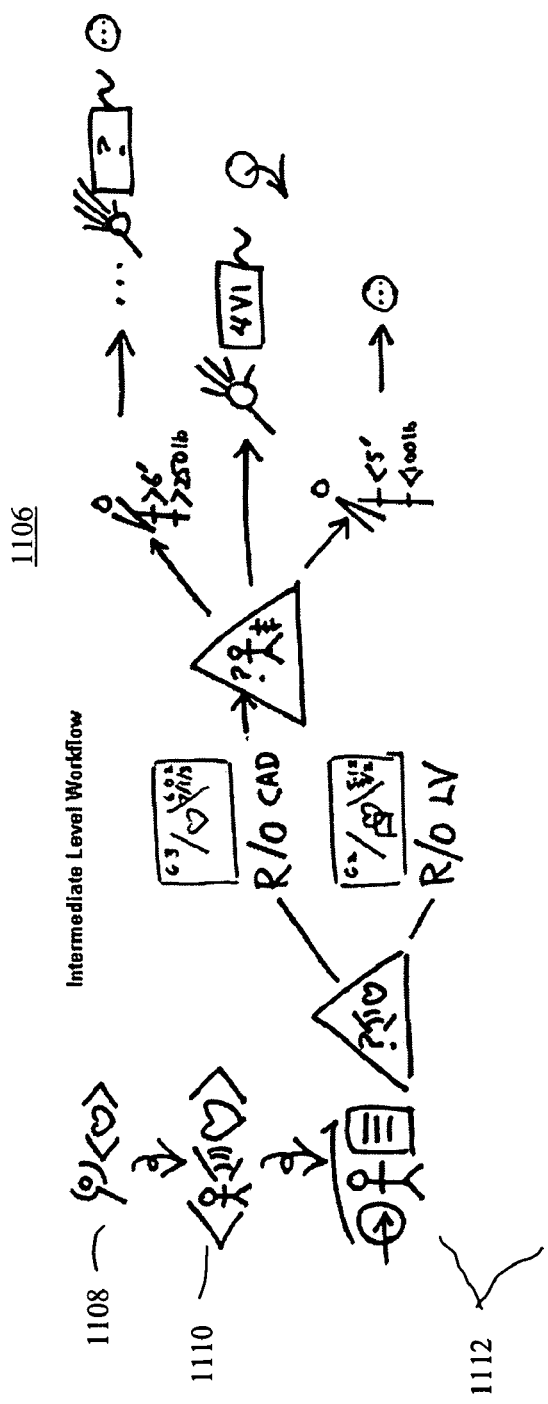
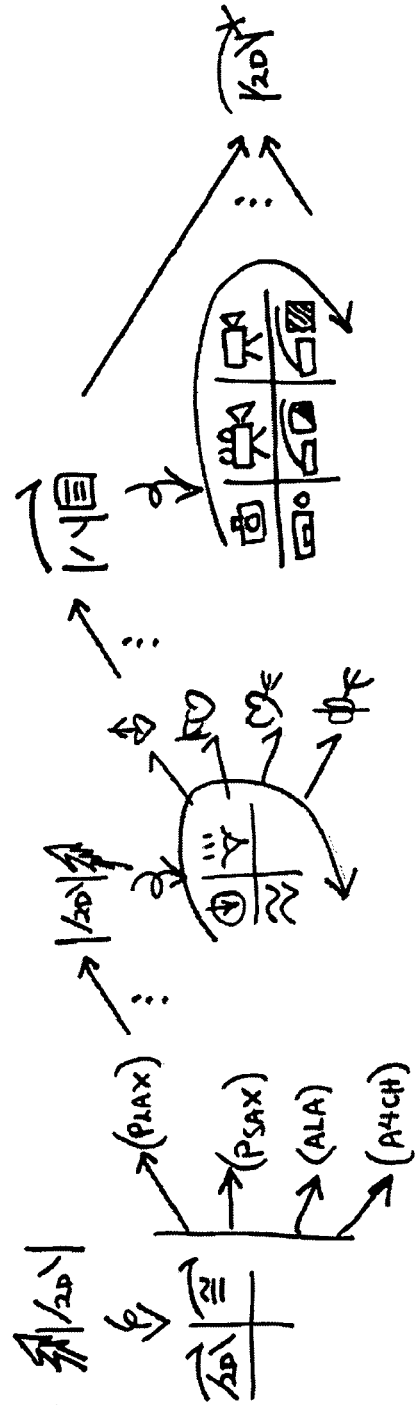

FIG. 11D

High Level View-Oriented Workflow

1114

FIG. 11E
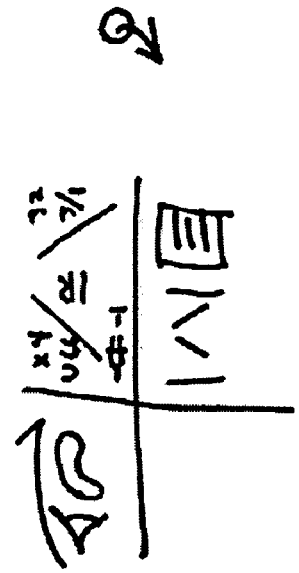
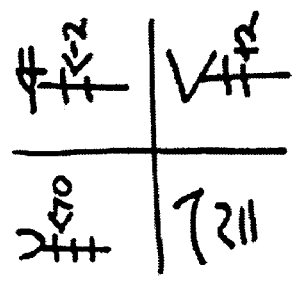
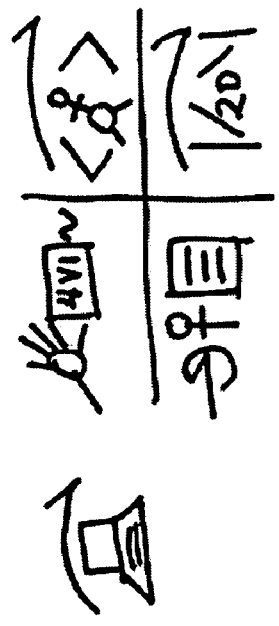
Contrast Study - Phrase 1 of 2

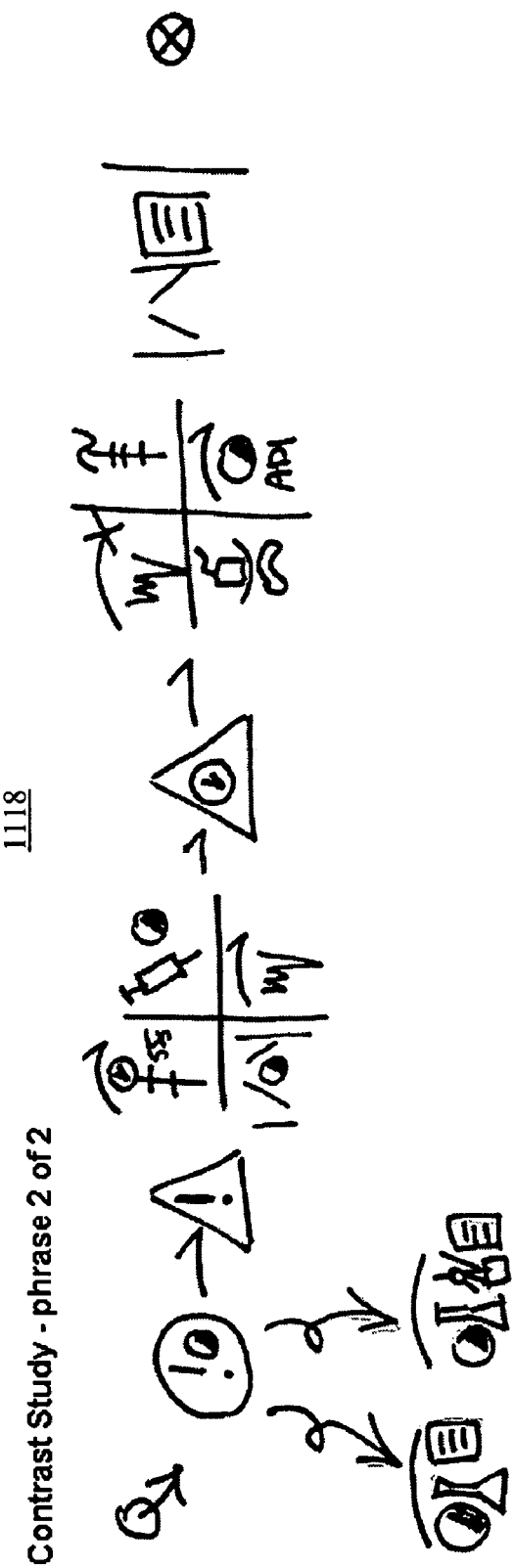

METHOD AND SYSTEM FOR DIAGNOSTIGRAPHIC BASED INTERACTIONS IN DIAGNOSTIC MEDICAL IMAGING

BACKGROUND

Describing and communicating diagnostic workflows for medical imaging, systems, such as diagnostic medical ultrasound systems, magnetic resonance imaging systems, etc., is often messy and time-consuming. Often methods are ad hoc or too far abstracted from the actual exam or workflow application to provide clear rigorous communications for all parties needing to understand the workflow description. Entities that have differing perspectives, such as caused by a language barrier, are unable to take advantage of a common core of meaning inherent in the workflow, leading to challenges in the creation and conveyance of the workflow instruction set. These entities may include doctors, clinicians and sonographers, administrative staff, application and equipment designers, engineers, test and service personnel, as well as, the diagnostic, acquisition, review systems and hospital enterprise systems with which they interact.

Using ad hoc workflow descriptions to perform exams can lead to inefficiency and safety concerns in performing workflow steps in the clinical environment and in the implementation of workflow related features, often requiring many supplementary details to determine the meaning of the workflow descriptions. In addition, the depiction and level of detail in one workflow description may be suitable for one user and not another. Further, even the same user, after some amount of experience with the system, may require a different depiction of the same workflow to carry out instructions efficiently.

Even more systematic approaches reveal significant limitations. Workflow management flow charts or process-oriented workflow descriptions require great effort to produce and are not easily understood "as-is" by many potential users of these workflow descriptions. Specific scenarios must be "translated" to workflow description documentation appropriate to the needs of important roles within the workflow. Workflow descriptions must be then translated into the spoken languages of target audiences, adding great cost to systems and documentation development.

Except in carefully designed systems the linkage between workflow descriptions and the command structure of the imaging system software and the functionality of imaging system hardware varies from application to application and relies on the expertise and understanding of clinicians, clinical engineers and system designers and support personnel. The challenge and resource demands of such development efforts often leave the creation of workflow materials to end users desperate for some guidance in navigating complex procedures.

Accordingly, there is a need for a more efficient system for communicating a workflow among the respective entities.

BRIEF DESCRIPTION OF THE DRAWINGS

FIG. 3 depicts exemplary activity check ideograms and conditional workflow indication ideograms according to one embodiment.

FIG. 7 depicts exemplary diagnostigram groupings for workflow elements relating to entity activities.

FIGS. 11A-11F depicts exemplary diagnostigraph sentences according to one embodiment.

DETAILED DESCRIPTION OF THE DRAWINGS AND PRESENTLY PREFERRED EMBODIMENTS

Figure 1:
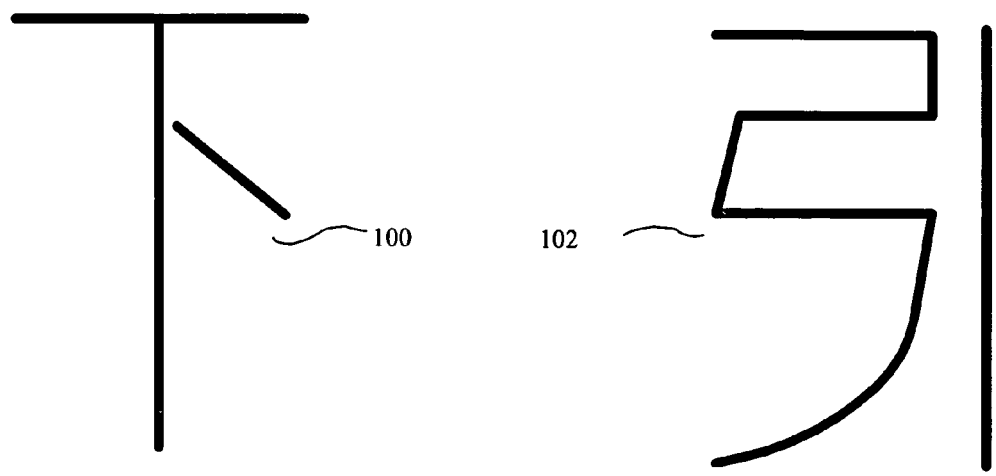
FIG. 1 depicts exemplary ideograms associated with a spoken language.

An ideographical language framework is disclosed that is designed to enable the description and communication of a series of workflow steps that is not dependent upon any particular natural language representation, such as spoken or written words. An ideogram is defined as a character or symbol representing an idea or thing without expressing the pronunciation of a particular word or words for it, i.e. not dependent upon a particular natural language representation. Further, as used herein, an ideogram may further be culturally independent as well. A workflow is defined as the activities, e.g. tasks or procedural steps, entities involved, i.e. actors or participants, such as people, organizations, machines, etc., inputs and outputs, states, requisite tools, and the relationships therebetween, for each step in a process. The various activities, entities, inputs, outputs, tools and relationships which make up the workflow are referred to as workflow elements. As will be described below, the disclosed embodiments represent workflow elements of a given workflow using ideograms meaningful to, i.e. commonly understood by, workflow participants, i.e. entities, and composed according to a simple syntax that enables easy recognition and use of a set of workflow instructions.

While the disclosed embodiments will generally be described with respect to workflows associated with diagnostic medical ultrasound imaging, such as examination workflows, training workflows, maintenance workflows, etc., it will be appreciated that the disclosed embodiments may be used in any application where a workflow may be communicated between entities, and all such applications are contemplated. Such applications may include other diagnostic medical imaging modalities, such as magnetic resonance imaging, X-ray, Computed Tomography, etc. Other applications may include manufacturing workflows, maintenance workflows, business process workflows, etc. in the healthcare industry or other industries. For example, other applications may include instructions for using or assembling consumer products.

In addition, while exemplary ideograms, syntax and relationships, grammatical or otherwise, therebetween, will be disclosed, it will be appreciated that the number, graphic appearance and/or interpretation of the ideograms, syntax or the relationships therebetween, are implementation dependent and may vary based upon the particular application and the entities involved.

The disclosed embodiments enable the users and designers of diagnostic medical ultrasound systems to use an ideographic language to communicate a series of workflow steps in a manner that is intuitive, efficient, non-ambiguous and customizable. Each element within the language has a pictographic representation and a specific, unambiguous meaning within the workflow task and can thus be displayed and printed as a graphic and still be mapped to machine implementation and to other places where rigorous definition is required. Elements are presented together as a syntactically composed set of pictures, and thus the depiction of this language is not dependent upon any specific natural language representation and is commonly and easily understood by a variety of users, despite language or other barriers to communication.

The disclosed embodiments, collectively referred to as "Diagnostigraphs" or "Diagnostigraph System", provide a framework for the development of a simple graphic language (or languages) with semantics specific to the problem of describing diagnostic ultrasound workflow scenarios (or workflow instructions in general) with mechanisms to assist users in following the set of instructions and other mechanisms to assist designers in creating or automatically generating such specifications.

As will be described in more detail below, the basic elements of the Diagnostigraph System are:

diagnostigram: A special purpose ideogram that incorporates a pictorial display and a precise meaning as a workflow activity or state with an internal structure that supports the ability to link that activity or step, sequentially or chronologically or hierarchically to others. It will be appreciated that the internal structure may support linking between activities or steps based on other relationships determined to be semantically relevant to a specific area of a specific Diagnostigraph system. A diagnostigram may be formal or informal. Formal diagnostigrams may further be associated to with a stickman-like notational element or "glyph" which is an informal abstracted representation of the diagnostigram designed for handwritten notation and/or communication in situations where full formal pictographic representations may not be practical. In addition, a diagnostigram may also be associated with a literal phoneme, which is a word or phrase that represents the diagnostigram, or meaning thereof, in the particular entity's language. The diagnostigram may further be associated with an ideographic phoneme which is a phonetic abstraction of the diagnostigram, or meaning thereof, i.e. the sound(s) associated with the meaning and may be thought of as an aural counterpart to the glyph. It will be appreciated a particular pictorial representation utilized as a diagnostigram by the disclosed embodiments may already have meaning and/or a representation in a particular entity's natural language. However, as part of the Diagnostigraph system, the pictorial representation is effectively accorded a secondary meaning, beyond any particular language, which is commonly understood by all of the entities. This secondary meaning may be similar to or different from the meaning ascribed by the particular entity's language and is not dependent upon any specific natural language representation;

diagnostigraph: A set of diagnostigrams (and/or glyphs) combined in simply constructed sentences (which are not flowcharts) to represent a workflow, workflow scenario, and/or portions thereof, that enable users to intuitively grasp the workflow task to be performed and enable dynamic transformation of the instruction set according to the needs of the user as well as the state of the system. A diagnostigraph may also be referred to as a diagnostigraph sentence or sentence; and diagnostigraph framework: a syntax, i.e. set of conventions and rules, for interpreting diagnostigrams alone and in the context of other diagnostigrams and for composing and interpreting diagnostigraph sentences, also referred to as a diagnostigraph syntax or syntax.

Diagnostigraph sentences are combined according to standardized syntax, described in more detail below, for arranging the pictorial elements according to their meaning and thus enable the representation and interpretation of workflow instructions at a variety of levels, supporting capture, communication and use of workflows, workflow scenarios and/or portions thereof.

The presentation of diagnostigraphs as an arrangement of pictures allows the diagnostigraphs to be natural-language-independent. Abstraction of the pictorial image elements supports the use of notations specific to the varying needs of users without introducing ambiguity.

The specific meaning attributable to diagnostigraphs within the workflow context allows mapping, in a straightforward manner, to software elements (data structures or objects), patterns of system output (keystroke or command logs), patterns of system input (disambiguated phonetic or mnemonic mappings).

When used in a diagnostic medical ultrasound application, a library of clear well-designed diagnostigrams and/or diagnostigraphs provides linkage between workflow descriptions and the command structure of the ultrasound system software and the functionality of ultrasound system hardware. Separation of this linkage from the ideographic core of the language makes the parts of this library, which embody the expertise and understanding of clinicians, clinical engineers and system designers and support personnel, portable from application to application, system to system, and clinic to clinic.

While many different approaches to communicating workflow steps have been devised by medical device manufacturers, hospitals and clinics, these prior approaches fail to combine the complete set of integrated functionalities provided by the Diagnostigraph solution of the disclosed embodiments.

One prior method of communicating the steps to perform specific scenarios within a workflow included taping pieces of paper with written notes to the ultrasound system monitor or keeping written notes in binders in exam room cabinets.

In addition there have been attempts on various ultrasound systems to provide on-screen workflow-related help for sonographers before and while performing an exam. Such help systems include schemes to provide linkage between system state and what operations are legal to perform given the current state. This concept has been developed through keyboard lighting (illuminating buttons or switches on the system to indicate they are okay to use in the given state), such as in the Sequoia and Aspen series diagnostic medical ultrasound systems, manufactured by Siemens Medical Solutions, located in Issaquah, Wash., and context sensitive menus of suggested next steps provided by a graphic user interface, such as in the Vivid and Logic 9 series diagnostic medical ultrasound systems, manufactured by General Electric Medical Systems, a division of General Electric, located in Waukesha, Wis. ("GE"). The GE Logic 9 supports context sensitive menus displayed on a dynamically-updated touch screen and may include decision support. Described using conventional text and widgets, these limited workflow support measures may be quite costly to develop and maintain. Deploying such systems in multiple linguistic environments across the globe involves many translations of complex collections of text.

Designers of ultrasound application workflow often employ textual scripts or flow-charting of scenarios using ad hoc or general process description diagrams to represent a series of states. Unfortunately, bridging the gaps between how clinicians and system designers use and understand an ultrasound workflow description generally involves a great deal of interaction—on the phone in meetings and working together with the system. While this interaction is valuable the results are often notes and reports that then have to be "translated" for others who need to understand the workflow.

The notes-near-the system method of workflow description, described above, has many obvious disadvantages including: forcing the sonographers to look back and forth between the screen and the notes. Further, the ad hoc nature of most such documentation and a perception that something the system should support is missing.

On-screen help has the advantage of being on-screen but there are still issues of disrupting the general flow of the exam or workflow to invoke and digest the help. Systems that are not inherently workflow based lack the coherence of scripted instructions.

In addition conventional workflow description methods offer no specific support for the capture and recording of workflow. Using textual scripts and process flow charts to describe workflow is almost completely unrelated to the built in support delivered with the systems.

General charting methodologies are overly abstract for describing clinical diagnostic scenarios on an ultrasound machine. While useful to trained designers and engineers they are not intuitive to clinicians or sonographers and do little on their own to bridge the ambiguities and conceptual gaps that occur as workflow descriptions move between the realms of engineers and clinicians (designers and users). Such charts are not the description of choice in most clinics for describing scripted exams nor are they easily mapped or translated to workflow-based ultrasound application control or feedback.

Process oriented methodologies, such as the Rational Unified Process ("RUP") promulgated IBM Corporations, located in White Plains, N.Y., or Integrated Definition (IDEF), in particular IDEF0 which specifies functional modeling, developed by Knowledge Based Systems Inc., located in College Station, Tex., describe workflows as coordinated sequences of activities, however they lack semantics specific to performing complex sequences of actions, such as those required by an ultrasound machine or to clinical diagnosis. While these methodologies employ a graphical framework, they still rely heavily on text and hence lack intuitive spoken language independence.

Context sensitive help menus and key highlighting to indicate workflow choices, while useful for hints or working through possible next steps in a procedure, tend to be lead to a jumpy or fragmented flow in actual use for completing an entire procedure. Generally, additional documentation is needed to provide either an overview or a more detailed view of the sub-steps within a procedure. Further, as hints or key highlighting are event driven, i.e., stimulus/response based, this type of workflow communication lacks the contextual elements necessary to convey an understanding to an entity of the overall design of the workflow or portion thereof or their position within a specific workflow as it is being performed.

The disclosed embodiments provide a framework for the development of a graphic language with semantics specific and suitable to a given application, such as the problem of describing diagnostic ultrasound workflow, with mechanisms to assist users in following the specification and to assist designers in creating such specifications. It will be appreciated that the application of diagnostigraphs to diagnostic medical ultrasound is but one exemplary application, that the disclosed embodiments have applicability outside of diagnostic medical ultrasound and that other applications of diagnostigraphs are contemplated. For example, other applications of Diagnostigraphs include other medical imaging modalities, such as Computerized Tomography, Magnetic Resonance Imaging, Positron Emission Tomography, Angiography, Radiation Therapy Planning and other noninvasive imaging modalities; electro-physiological studies, surgical algorithms and protocols, guided biopsies (i.e. for breast cancer) and other invasive medical procedures; combined diagnostic modality procedures, combined therapeutic and diagnostic modality procedures; industrial procedures such as manufacturing control procedures, process control procedures, training procedures, software development process control procedures; safety procedures such as airplane cockpit check, dive planning check; security procedures such as airport security checks; enterprise workflows such as payroll procedures, employee processing procedures, patent application procedures; general instructional procedures such as cooking recipes and tax preparation procedures; consumer procedures such as consumer home product assembly or maintenance (i.e. putting together a bicycle, activating your cell phone, installing your home computer); any workflow or procedure that involves a sequence or sequences of steps to be performed, including sports training, choreography, cinematography, military logistics, large machine installation, building construction, building maintenance, government service administration, etc.

Diagnostigraphs offer several methods for capturing and recording workflows and the constituent elements thereof. Glyphs, also referred to as "Stick-man", i.e. simplified pictorial notations for common diagnostigrams, may allow a designer or clinician to quickly jot down diagnostigraph sentences. Glyph notation may be thought as the "cursive script" representation of the "typeset" diagnostigram graphic, i.e. both designate the diagnostigram's meaning, as described above. While the glyph notation may be more cryptic, it has the advantages of being quick and easy to jot on a piece of paper, however its content may be less evident to an unintended casual observer outside the group of entities. Diagnostigram graphics kept as part of a drawing library may enable higher quality documentation of the captured instructions. Diagnostigraph-based systems also support ideographic linkage between its ideogram and the associated meaning or connotation. The meaning and hence the graphic can be invoked using specific verbalizations bound to the ideograms meaning that could be typed in or spoken. These specific input mappings can be used for the quick consistent capture of workflow steps that can be immediately displayed or incorporated visually, aurally or programmatically into an ultrasound system. For example, two useful such auditory mappings are the "Literal Phonetic Mapping and the "Ideographic Phonetic Mapping", described above, which may be associated with a particular diagnostigram. The Literal Phoneme is a word or phrase that represents the Diagnostigram in the user's language. It can be thought of a translation of the Diagnostigram's meaning into words or phrases the user can easily understand. The Ideographic Phoneme is a sound or sounds associated with the Diagnostigram's meaning—it is intended to be universal and not language specific, although local, site-specific or voice-recognition specific overrides, aliases or extensions are allowed. The Ideographic Phoneme is intended as a phonetic abstraction of the Diagnostigram in much the same way as the "Stickman" or glyph notation is a visual abstraction of the Diagnostigram.

Diagnostigraph sentences and their elements are specifically designed to represent complete and meaningful segments of the workflow. The level of abstraction can be validated to determine that they are intuitive to users. The state frame of a diagnostigraph pertains to exactly what the user is doing or will be doing next with explicit graphics that depict what activities need to be carried out at a level of detail suitable to the user. Diagnostigrams can be linked to system functionality and relevant help as a generated software object.

In addition to these comparative advantages, the disclosed embodiments offer a wide range of potential advantages, inconceivable within the constraints of usual workflow description methodologies. As discrete elements within a diagnostigraph, diagnostigrams enable the system to track usage and thus suggest or even perform optimizations of the workflow (described in more detail below).

As described above, an ideogram is a graphic with an assigned meaning or a symbol used in a writing system to represent an idea or thing without expressing a particular word or phrase for it. FIG. 1 shows exemplary ideograms from the Chinese language. In particular, FIG. 1 shows the Chinese characters for "to go down" 100 and "to pull" 102 (think of pulling the string of a bow). Ideographic languages combine simple pictorial characters to represent more complex concepts. As natural ideographic languages evolve, these "graphics" are often reduced to simple stylized indications of the original picture. For spoken languages, ideographic characters are composed into sentences according to the underlying natural language syntax of the spoken language.

Diagnostigrams are ideograms specifically created to communicate workflow elements (activities and states) and are composed into sentences according to the underlying syntax of workflow implementation. Because they are designed to be grasped quickly, with minimum training, diagnostigrams will generally be more narrative and pictorial than ideograms used to represent spoken language. It will be appreciated that the level of abstraction of the pictorial image is implementation dependent.

Diagnostigrams can be combined to represent complex workflow activities and states. Diagnostigrams can be composed into sentences according to the underlying behavior of the workflow being represented using a set of conventions, i.e. syntax, called the diagnostigraph framework. The basic compositional elements of the diagnostigram framework are area markings, grouping and compositional markers, e.g. grids, also referred to as transformation grids, and frames, also referred to as target frames, that hold ideographs for activities and/or states, and direction markings (arrows and conventions, such as arrangement conventions, indicating the order in which the sentence elements must be read). Additional syntax and rules according to the demands of a specific workflow application may be added as extensions using special purpose Diagnostigrams, as will be described below.

As described above, diagnostigraph-sentences are composed of workflow elements and structural notation, all represented by diagnostigrams. Workflow within the diagnostigraph framework is a sequence of activities performed to achieve one or more objectives. As will be described below, some workflow elements and their associated diagnostigram may actually be decomposed into multiple workflow elements and associated diagnostigrams, depending upon the need for detail or the level of competence of a given entity. Structural notations (diagnostigrams) within the diagnostigraph sentence may denote a more detailed sequence of activities/elements, e.g. as a separate diagnostigraph sentence, that a specific "high-level" diagnostigram in the Diagnostigraph workflow sentence represents, e.g. may be decomposed into. This separate sentence is conceptually orthogonal to the conventional direction of the workflow sentence and is possibly denoted in the primary diagnostigraph by "Drill down" or "Implementation" diagnostigrams which indicate that the entity is to look to this separate sentence to accomplish the multiple workflow tasks indicated by the high-level diagnostigram. This structure offers the more competent entity, one familiar with the workflow element indicated by the high-level diagnostigram, to ignore the separate sentence comprising the decomposed workflow elements where the entity is already familiar with the elements, thereby allowing more competent entities to create and/or use more compact sentence structures, while not inhibiting interpretation by less competent entities. Further, this structure permits efficient use of the different communications media over which diagnostigraphs may be communicated. Diagnostigraph sentences are generally constructed from transformations (Grouped Diagnostigrams or Transformation Grids) connected to goal states (Target Frames).

An exemplary framework syntax includes an alternation of Transformation Grids and Target Frames using transform verbs, such as arrows, that can include post-conditions (Activity Checks) and pre-conditions (State Checks). As will be discussed, a diagnostigraph is not limited to an alternating sequence but may include an uninterrupted series of transformation grids, etc., with or without target frames.

Figure 2:
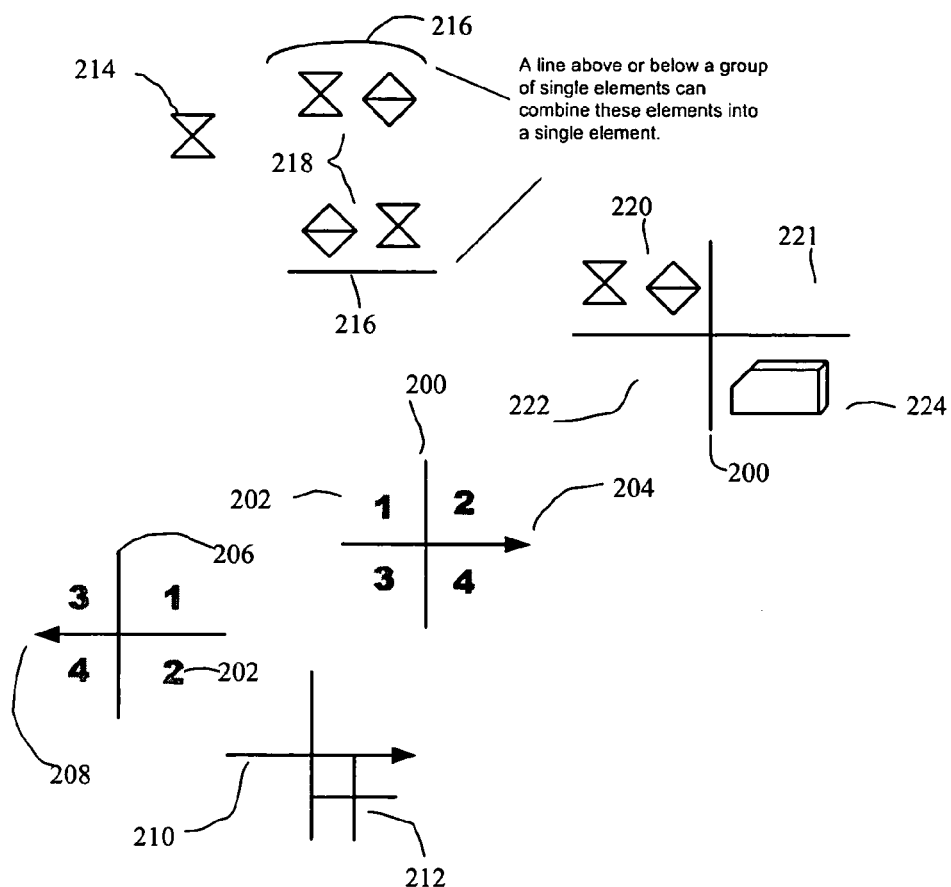
FIG. 2 depicts exemplary transformation grouping and grid ideograms according to one embodiment.

FIG. 2 shows exemplary ideograms of a workflow transformation element 214, a transformation group 218 and a transformation grid 200. An ideogram may represent a single workflow transformation 214 and several of these elemental transformations may be grouped to indicate composite or alternate workflow transformations 218, such as by obvious visual interrelatedness or by the use of a grouping mark 216. Context and ordering may affect the meaning of such groupings. Multiple single elements and/or groupings may be organized utilizing a transform grid 200. The grid 200, depicted in this embodiment as a 2×2 matrix (other than 2×2 matrices are also contemplated) includes four quadrants 202 and a direction indicator 204. The transformation element 214, grouping 218 or grid 200 holds one or several workflow activities represented by a combination of meaning outlines and pictures or characters that display the action's meaning. The grid leads to a system state or clinical objective, represented by a frame that may appear as an abstraction of Ultrasound machine's screen or some other meaning outline and graphic that represents the achieved objective, described below in relation to FIG. 4. In one embodiment, all workflow steps indicated in the transformation grid 200 must be complete before achieving and/or moving on to the next transformation grid 200 or goal/objective (described below).

Each quadrant 202 of the grid 200 may hold zero 221, one 224 or more 220 ideograms (more than two possible but not shown). The entity reads the ideograms of each quadrant 202 in an order specified by the diagnostigraph framework/syntax. As shown in the figure, in one embodiment, the grid 200 is read in a manner like reading words on a page conventionally in Western cultures from left to right and from up to down starting with the upper left quadrant 202, however, as shown by grid 206, other starting quadrants may be specified or even other orderings, such as from up to down and from right to left. In alternative embodiments, the ordering may be clockwise or counter-clockwise. Further, multiple orderings may be specified by the framework and identified by an indicator represented on the transformation grid pictogram (not shown). In an alternative embodiment, a transformation grid 210 may include sub-grids 212 which contain ideograms indicating sub-steps of the workflow or workflow steps to be performed in parallel with other workflow steps (see also FIG. 3 304). The basic rule of organization is to model an abstraction of the entity's perception of visual flow, and may be thought of as areas demarcated by invisible boundaries that comprise virtual panels, similar to the panels of a comic strip or comic book, arranged such that the user can naturally/intuitively follow the flow of events and structure. Such an arrangement may be sequential, parallel, hierarchical or combinations thereof.

As shown in FIG. 2, a single diagnostigram 214 may represent a transformation. In alternative embodiments, a diagnostigram of a line 216 placed above or below a group of single elements 218 may indicate to combine the elements 218 into a single high-level element (not shown). Further, multiple single diagnostigrams 220 and groupings may be organized within grid 200 for readability, etc., with no additional grouping indications being required.

FIG. 3 shows other exemplary ideograms. For example, a simple transformation ideogram 308 is depicted as consisting of an arrow which indicate a transition from one activity to another activity. Further ideograms 300 302 are shown which indicate an activity check or state check 300 coupled with an ideogram of a transformation grid 200 and transition 308. Herein, the phrase "coupled with" is defined to mean directly connected to or indirectly connected through one or more intermediate components. Such intermediate components may include both hardware and software based components. When the activity check 300 follows a transformation grid 200, this indicates that the condition is a post condition that should have occurred based on the execution of the workflow steps indicated in the transformation grid 200 or a condition that will occur and the entity is to wait for its occurrence. Alternatively, the activity check 300 may indicate a condition that may occur but the entity need not wait for the occurrence before continuing on with the workflow. When the activity check 302 precedes a transformation grid 200, this may indicate that entity is to wait or check for the indicated condition before proceeding. The ideogram representing the activity check 300 302 may be further subdivided 306 to allow for more complex specification of conditions. Other exemplary syntax extensions are also depicted showing different ideograms, alone and in combination, to indicate various scenarios. For example, workflows may divide at a specific point in the workflow into a distinct or separate sequence or set of subsidiary workflows. Such as division may be indicated by a single flow indicator, i.e. arrow, pointing to a line (perpendicular to the arrow's shaft), or otherwise indicating, from which several flow indicators, i.e. arrows, emanate 320. Each of these emanating arrows 308 may point to a different workflow sentence 328, e.g. diagnostigraph sentence, or portion thereof. In the case where each of these subsidiary workflows 328 is identical but for a specific parameter 332 this may be represented an ellipsis ideogram 322. As another example, activity checks 300 or state checks 302 may lead to a set of alternative workflows 312, based on a result or condition, and this may be indicated by a set of arrows/indicators 308 emanating from the check 300 302, each pointing to a diagnostigraph sentence or portion thereof (not shown) related to one or more of the possible conditions determined by the check 330.

Another common case occurs when one or more general activities are repeated throughout a diverging set of workflows. This may be indicated by an arrow 326 curving around a transformation grid 200 that contains the repeated activities, with arrows 308 possibly emanating from the curving arrow 326 pointing to a diverging set of workflows to which this general repetitions of actions pertains. Branching 326, conditional 312 and general repeating 316 divergences in this embodiment are represented by arrows 308 fanning out away from the starting point of divergence. The merging of these diverging workflow sentences 328 back to a single workflow sentence 328 may be indicated by an ellipsis between a set of arrows 328 pointing to the point at which the single workflow 328 resumes.

Figure 4:
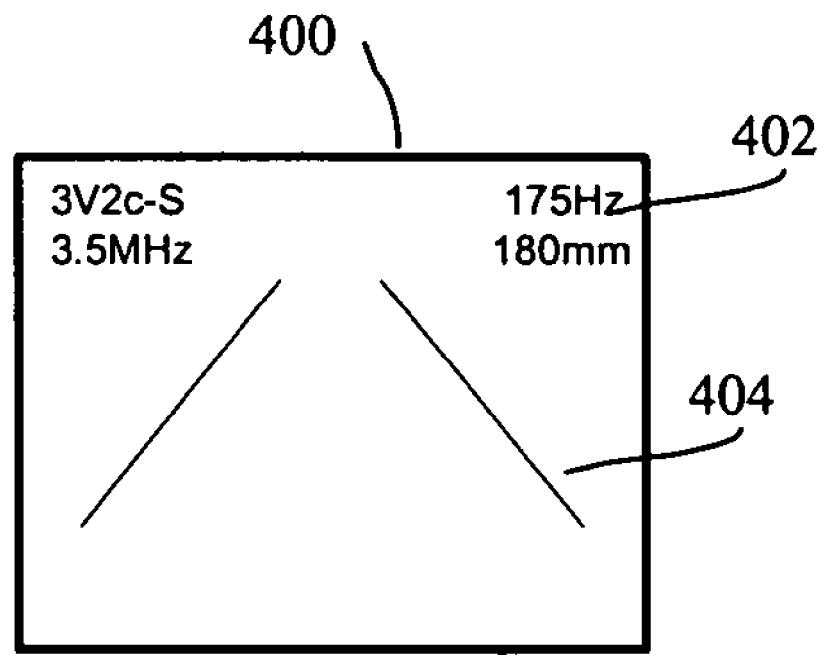
FIG. 4 depicts exemplary target frame ideograms according to one embodiment.

FIG. 4 shows an exemplary ideogram of a target frame 400 indicating a goal or objective state. In the figure, the exemplary ideogram 400 is representative of a screen display of a diagnostic medical ultrasound system indicating to the entity that the screen of their system should have similar appearance. State indications 402 within the target frame 400 may be text as it would appear on a screen with which the user is familiar or may be abstracted to a diagnostigraph 404. Other ideographic representations of goals or objectives may be used, for example simple data readouts or a voice readout describing the expected state. Target frames may simply represent an expected state and thus function as a progress check or may be combined with special diagnostigrams to represent a condition or set of conditions required for verification of a workflow step necessary before progressing further.

Figure 5:
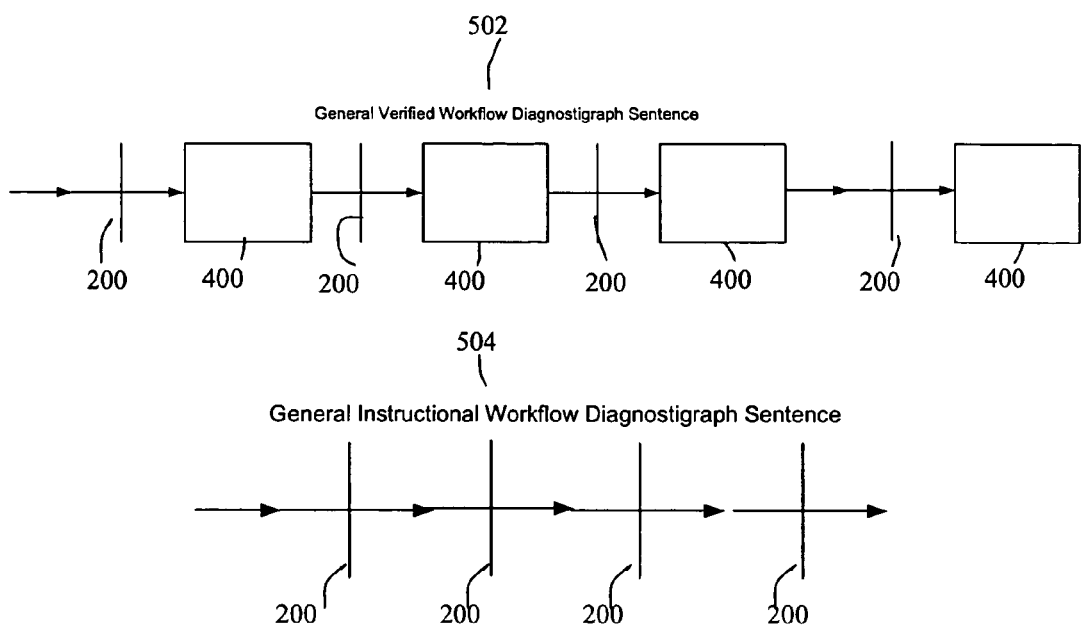
FIG. 5 depicts the structure of two exemplary diagnostigraph sentences using the ideograms of FIGS. 2 and 4 according to one embodiment.

FIG. 5 shows an exemplary structure of a diagnostigraph sentence 502 according to one embodiment. In the example, the sentence 502 includes alternating transformation grids 200 and target frames 400 indicating that the entity is to perform some workflow steps to achieve a particular goal and the perform additional steps to reach the next goal. It will be appreciated that other sentence structures are possible including sentences having multiple transformation grids 200 or target frames 400 in sequence, sentences including parallel activities, sentences including only target frames 400 or sentences 504 including only transformation grids 200 (possibly referred to as "instructional" sentences), and sentences which include other constructs such as activity checks 300 or other extensions to the diagnostigraph framework. In an instructional workflow 504, implied target states may be the entity's observations or understandings as the workflow is performed or read.

Within the framework, workflow item/element ideograms (diagnostigrams) are the items used to build structured graphical sentences under the framework following rules that make sense for the workflow task being described.

Figure 6:
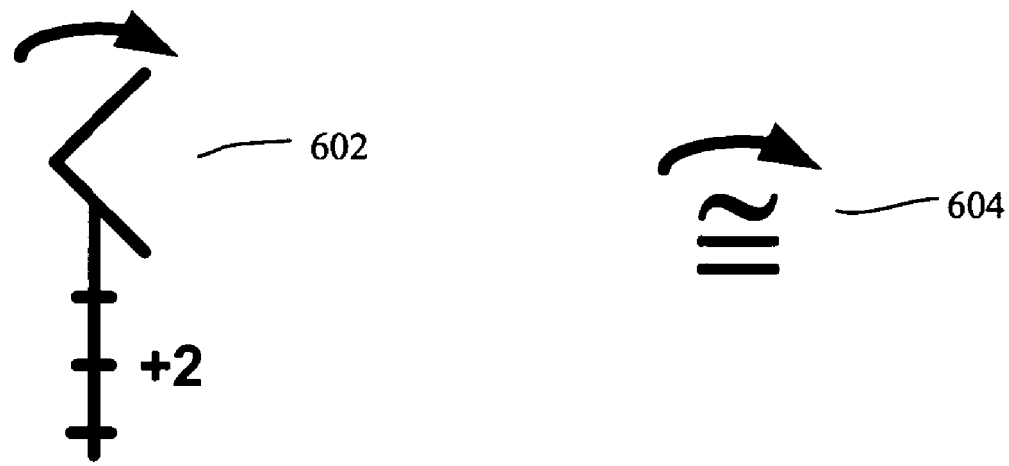
FIG. 6 depicts exemplary diagnostigrams for workflow elements.

FIG. 6 shows exemplary diagnostigrams 602 604 indicating particular workflow elements of a diagnostic medical ultrasound workflow. Diagnostigrams can represent simple workflow elements, such as <Set Gain up 2> 602 or <Turn on Tissue Equalization> 604. They can be pure graphics or meaningful graphic outlines with text and numbers (annotated meaning outline). In cases where universally understood, language-specific acronyms exist, as described above with respect to ideograms which have acquired a commonly understood secondary meaning, they may be used defined and used as a Diagnostigram (i.e. "R/O" for "rule out" is the standard notation a sonographer would expect when checking Cardiac Indicators to determine a subsequent course of action no matter what language they speak). An exemplary library of diagnostigrams is described below.

As described above, diagnostigrams can be combined into groups that can be represented and replaced by a higher level diagnostigram that makes sense to the user and that enables both intuitive grasping of a whole sequence of operations and the ability of a user to drill down to important details and conditions that underlie the group item. This also allows quick high-level transcription of workflow with implied details to be supplied later. Entities with limited capabilities can access the detailed diagnostigrams when necessary.

FIG. 7 shows other exemplary diagnostigrams 702 704. In one embodiment, diagnostigrams which indicate an actual activity or state of a workflow are essential. For example, <Enter Patient Data> 702, <Enter Measurement Data> 704 or <2D Image is Displayed> (not shown). An essential Diagnostigram is referred to as a base diagnostigram and may have many maps to relate it to how it will be used or displayed.

In a hierarchy of diagnostigrams where one diagnostigram (a collective, general or group diagnostigram) may be decomposed into or indicated by multiple other diagnostigrams (constituent or specific diagnostigrams), composition mappings provide a path from a more basic diagnostigram item to the group diagnostigram it belongs to and from the group to its constituents. In one embodiment, a given diagnostigram may be decomposed into constituent diagnostigrams directly mapping to the command structure or key presses on the Ultrasound machine itself, (which could enable an animated diagnostigram sentence to actually perform some of the steps of the exam under the guidance of the sonographer). An alternative composition mapping is for a single diagnostigram to map to an entire diagnostigraph sentence.

Representational Mappings provide a way to link a Diagnostigram to other representations. They include input and output mappings. In one embodiment, the most significant diagnostigram output map is the Diagnostigram's Graphic Mappings, which links a diagnostigram to various pictorial or notational representations (bitmap, gif, line rendering, stickman etc.) used to display the activity or state. Other output maps could include audio output, composed workflow logs, communication to other systems or users to notify when target frames are reached. Activity diagnostigrams or transform grids can be linked to the actual system state to enable interaction with acquisition or display parameters.

The base library of Diagnostigrams and mappings may be extended to support uses for a variety of workflow applications and particular user sites may have extension libraries for custom workflow applications. These can include activity, state or syntax extensions.

The concept of Diagnostigraphs and Diagnostigrams is essentially simple but scalable. The simplest implementation of the framework can focus on the depiction and communication of specific well-known workflows to build up the initial library and verify the effectiveness of initial descriptions.

Advantages may be found even with even a small "Stickman" library in improving communication between clinical experts and engineers. Creating a basic software widget for displaying several specific exam workflows would involve no more than a normal sized feature project. Implementations can be used internally and tested incrementally and built up to a complete workflow support system.

Clear graphics and standard syntax for combining graphics enable representation and interpretation at a variety of levels, and supports capture, communication and use of workflow scenarios. In one embodiment, diagnostigram sentences could be tested by displaying them without explanation to a group of target users and have them attempt to perform or describe what needs to be done. Any confusion or indecision would indicate inappropriate graphics or ideograms or missing steps in the scenario.

Thus a useful library of basic elements and workflow scenarios may be developed that would support wide reuse within varying medical enterprises. Once the initial library is created it would be immediately usable and reusable but ongoing statistical feedback mechanisms built into delivered diagnostigram software and customization might be employed, to allow continuous improvement and extension of the diagnostigram library.

Figure 8:
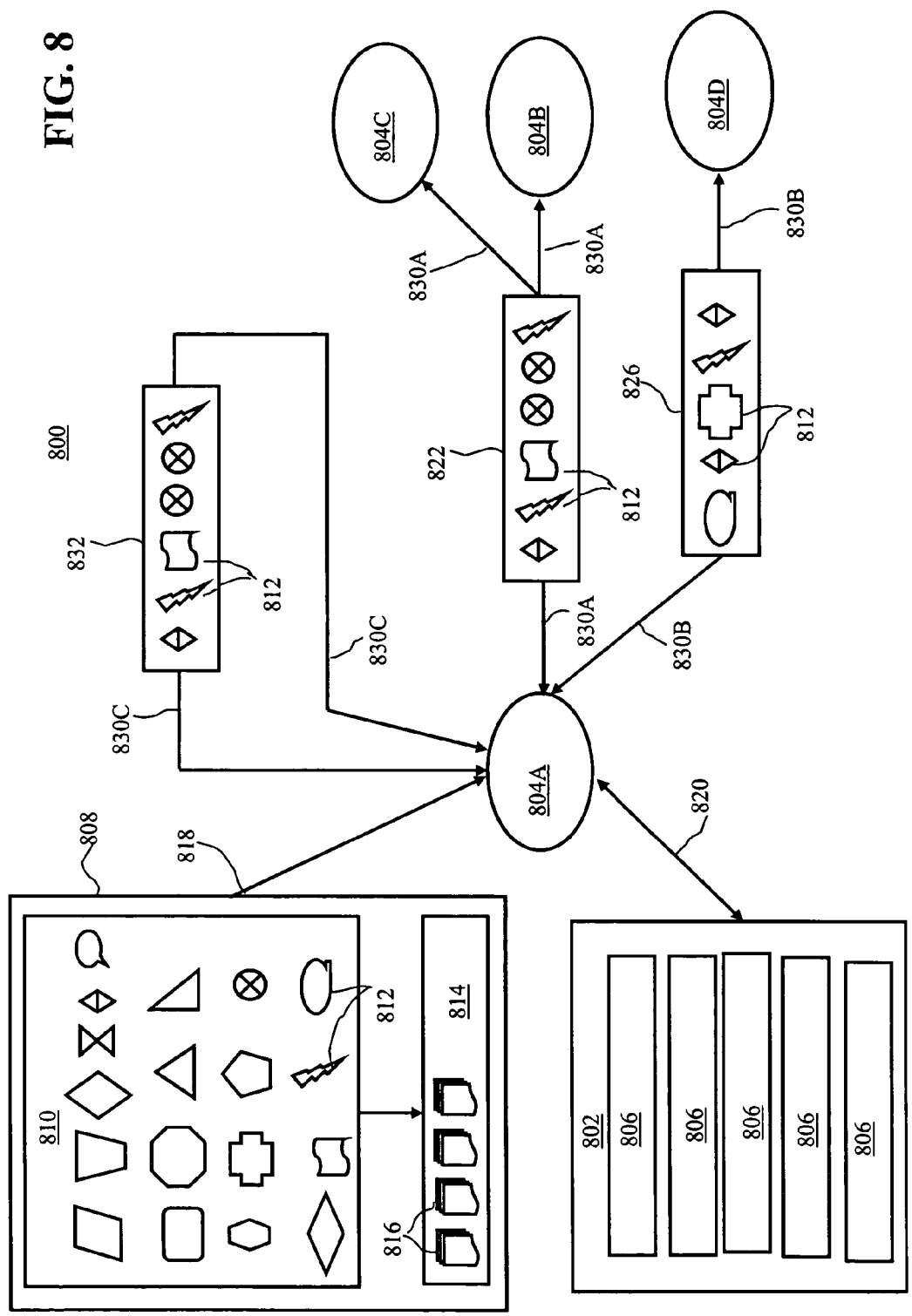
FIG. 8 depicts a block diagram of exemplary system for communications of a workflow between entities according to one embodiment.
Figure 9:
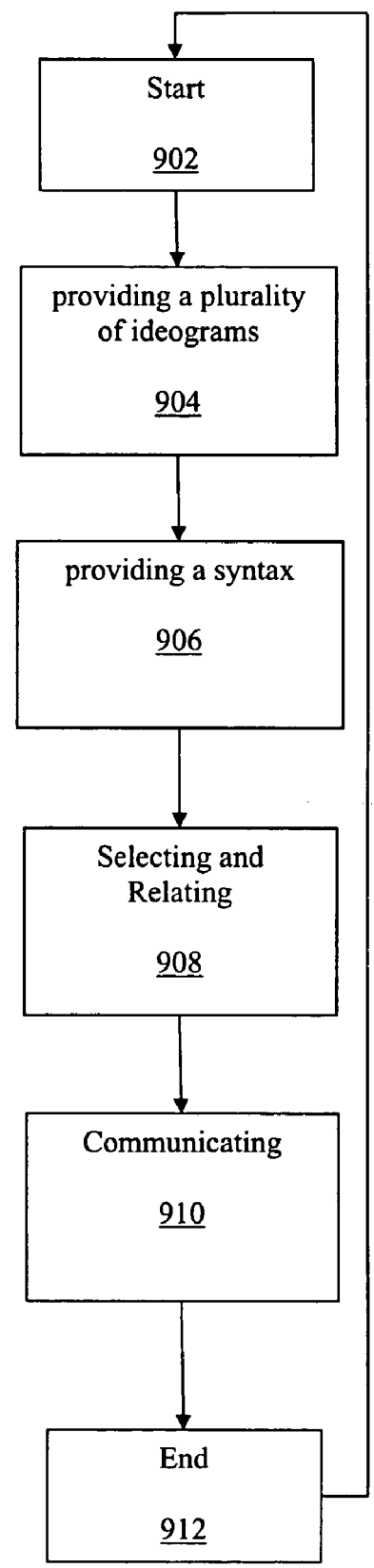
FIG. 9 depicts a flow chart detailing the use of diagnostigraphs to express a workflow.

FIGS. 8 and 9 depict a block diagram 800 and flow chart of an exemplary system 808 for communications of a workflow 802 between at least two entities 804A-D according to one embodiment. The system 808 may be used as a method of communicating the workflow 802 from one entity 804A-D to another entity 804A-D, as a system for interacting, e.g. exchanging ideas, between entities 804A-D, as a system for expressing workflows 802, as a system for directing one entity 804A-D in the performance of a workflow 802 by another entity 804A-D, as a system for instruction or demonstration of a workflow 802, as an input system to a device, such as a diagnostic medical ultrasound system, as a system for generating output from a device, or combinations thereof. The workflow 802 includes a subset of one or more workflow elements 806, described above, taken from an overall selection of workflow elements (not shown), i.e. all of the possible elements the workflow could include. A given workflow 802 may only include a subset of the steps, functions, actions, etc. which may be available for the construction of all of the possible workflows. Workflow elements include acts, objectives, events, or the relationships between them, or combinations thereof, as was described above. In one embodiment, the workflow 802 is a diagnostic medical ultrasound workflow 802 such as an examination or maintenance workflow 802.

One or more of the entities 804A-D may include users of the workflow, such as sonographers, radiologists, or maintenance technicians, creators of the workflow, such as ultrasound manufacturers, clinicians, etc., and/or instructors who teach users to create or implement workflows. One or more of the entities 804A-D may further include a computer, or graphic user interface thereto, a diagnostic medical ultrasound system, medical review station, handheld computer, cellular telephone or personal computer, in addition to designers, creators, or general users of such systems, or combinations thereof. It will be appreciated that one or more of the entities 804A-D may include any entity or device which is a participant, in some manner, in the workflow. In particular, for diagnostic medical ultrasound workflows, the entities 804A-D may include a sonographer, clinician and diagnostic medical ultrasound system, including image acquisition software, diagnostic software, medical examination software, medical study review software or some form of database, such as a medical history database or system log. Further, it will be appreciated that the two entities may actually be one in same, acting either in the same or a different role. For example, the disclosed embodiments may be used by a sonographer to capture notes to themselves or for archival purposes, or an ultrasound machine may utilize the disclosed embodiments as a method of storage for later retrieval, etc.

The system 808 includes a plurality of ideograms 810, also referred to as diagnostigrams, where each 812 of the plurality of ideograms 810 comprises a visual indication of at least one workflow element 806 of the plurality of workflow elements and capable of conveying a connotation, e.g. a suggestion of a meaning beyond any explicit denotation or description, of the at least one workflow element 806 to the at least two entities 804A-C, i.e. the connotation is commonly understood by the at least two entities 804A-C. Further, the connotation is not dependent upon any specific natural language representation of the at least one workflow element 806 (block 904 of FIG. 9) although it may be associated with such a representation. Each of the plurality of ideograms comprise an unambiguous, e.g. commonly understood, interpretation among the communicating entities 804A-D, i.e. normalizes the interpretation to a common understanding between the entities 804A-D. In one embodiment, there is at least one ideogram 812 for each possible workflow element 806. As described above, in alternative embodiments, additional ideograms 812 may represent multiple workflow elements 806 and may supplement or replace the individual ideograms 812 which represent the individual workflow elements 812. The interpretation of the additional ideograms 812 may be indicated by a combination of at least two other constituent ideograms 812 of the plurality of ideograms 810 and the additional ideogram 812 may visually refer to the combination. In an n alternative embodiment, each of the plurality of ideograms 812 may further comprise a verbalization in one or more spoken languages. Further, the ideogram may comprises one verbalization when the ideogram 812 is used alone and another verbalization when the ideogram 812 is used in combination with another of the plurality of ideograms 810. In addition, any ideogram may have alternate verbalizations, when useful, for communications between certain entities 804 A-D.

The plurality of ideograms 810 may include at least one action ideogram 812 comprising a visual indication of at least one of a plurality of acts to be performed by at least one of the at least two entities 804A-D. In one embodiment, the acts may include an act of verifying a condition, such as verifying that a condition as or will occur. In an alternative embodiment, the acts may include inaction.

The plurality of ideograms 810 may also include at least one objective ideogram 812 comprising a visual indication of at least one of a plurality of objective, e.g. a target frame described above. Each of the plurality of objectives may include at least one goal related to the performance of at least one of the plurality of acts. In one embodiment, the particular goal may be something to be avoided rather than achieved by the particular entity. In another embodiment, the goal may include an expected result of the performance of one of the plurality of acts. In an embodiment related to diagnostic medical ultrasound wherein one of the entities 804A-D includes a diagnostic medical ultrasound system, the goal may include a particular state of the ultrasound system, such as a mode of imaging to be achieved by the act of turning-on a particular-setting. An objective ideogram may a visual representation of a visual appearance of the at least one of the plurality of objectives. For example, an objective ideogram may comprises a visual representation of a computer screen display or other data output device, the appearance of which is the goal that the entity should achieve. Where an objective ideogram 812 is preceded by at least one action ideogram 812 in the representation of the workflow 802, the objective ideogram 812 may further include a visual representation of a state achieved via execution of all of the plurality of acts represented by the at least one action ideogram 812. In an alternative embodiment, a single ideogram 812 may indicate and/or imply both one or more actions and indicate and/or imply one or more objectives to be achieved by those actions.

The plurality of ideograms 810 may also include at least one event ideogram 812 which comprises a visual indication of an expected event caused by an entity other than the at least two entities. For example, the patient undergoing ultrasound examination may take some action or a network disconnect event or other unexpected system error or malfunction, may lead to the selection of an alternative workflow.

The plurality of ideograms 810 may also include relationship ideograms 812, described in more detail below, for communicating syntactical nuances of the other ideograms 812.

The system 808 also includes a syntax 814 defining interpretation of each ideogram 812 of the plurality of ideograms 810 alone and/or in combination with at least another 812 of the plurality of ideograms, the syntax operative to allow selection and relation of a subset of the plurality of ideograms 810 by one of the at least two entities 804A-D to represent the workflow 802, or a portion thereof, to another of the at least two entities 804A-D (block 906 of FIG. 9). The syntax 814 is also referred to as the diagnostigraph framework. In particular, the syntax may include rules and conventions 816 which define interpretation of the plurality of ideograms 810. The syntax 814 may rely on relationship ideograms 812, as described above, which comprise a visual indication of a relationship between at least two of the plurality of ideograms, such as a visual indication of ordering. Ordering of ideograms for purposes of interpretation may be one of sequential, linear, discontinuous, circular, parallel, structural, hierarchical, temporal or combinations thereof. Exemplary relationship ideograms include transformation groups 218 or transformation grids 200 shown in FIG. 2 and described in more detail above.

For example, wherein an action ideogram which represents the act of verifying a condition precedes another action ideogram, a convention 816 of the syntax 814 may define that performance of the act visually indicated by the subsequent action ideogram is dependent upon the verification of the condition. The convention 816 may further define that the entity 804A-D wait for the condition to occur or verify that the condition has occurred, depending on the order in which the verifying ideogram 812 appears in relation to another action ideogram 812. If the verifying ideogram 812 precedes the action ideogram, then the entity 804A-D must wait for the condition to occur and if the verifying ideogram 812 follows the action ideogram 812, the entity 804A-D must verify that the condition has occurred.

The conventions 816 of the syntax 814 may further define contextual interpretations of ideograms 812 such where an interpretation of each ideogram of the plurality of ideograms may be altered by the context in which the ideogram is utilized. In one embodiment, the syntax 814 defines that each of the plurality of ideograms 810 has a first interpretation when utilized alone and a second interpretation when utilized in combination with at least one other ideogram 812. The second interpretation may be more specific than the first interpretation, broader than the first interpretation, or the opposite of the first interpretation.

In operation, a first entity 804A wishes to communicate the workflow 802, or portion thereof, to a second entity 804B. The first entity 804A creates a set 822 of ideograms 812, e.g. a diagnostigraph sentence including diagnostigrams as described above, selected from the plurality of ideograms 810 based on the syntax 814 and the elements 806 of the workflow 802 (block 908 of FIG. 9). The set 822 of ideograms 812 indicates the workflow 802 and its constituent elements 806 as described above. The first entity 804A may create the set 822 using a computer which includes the ideogram library as a database and a word-processor-type program which allows the entity 804A to construct sets 822 of ideograms based input of the workflow 802 elements 806. In other embodiments, the entity 804A may simply jot various ideograms 812 onto a sheet of paper based on his memory of the plurality of ideograms 810 and syntax 814. Still in other embodiments, the set 822 of ideograms 812 may be created by an automated system, which is the first entity 804A, such as a computer system or suitably programmed diagnostic medical ultrasound system, based upon input of the workflow 802, manually or automatically, such as from an activity log of historical activity on the system. In generating the set 822 of ideograms 812, the automated system may refine the workflow elements 806 to accomplish the workflow in a more efficient manner or to adjust the depiction of the workflow to the competency level of the entity 804B who will receive the set 822.

The set 822 of ideograms 812 is then communicated to the second entity 804B, and possibly to a third entity 804C, via a communications medium 830A (block 910 of FIG. 9). The communications medium 830A may be any form of communications between the entities 804A, 804B, 804C, such as exchange of paper, oral dialogue (via direct interaction or electronic communications), facsimile, digital recognition and/or transmission, aural recognition, telephonic communications, etc.

Upon receipt of the set 822, i.e. diagnostigraph sentence, of ideograms 812, the receiving entity 804B may act on the indicated workflow 802, such as by implementing the workflow 802 indicated by the set 822 of ideograms, communicating the set 822 to another entity, modifying the set 822, etc., or combinations thereof. In implementing the workflow, the set 822 of ideograms 812 directs performance of the workflow without disrupting the performance. Where interaction is possible, an entity may also use sentences composed of special inquiry diagnostigrams to compose sentences, returned to the sender to provide feedback or request clarification or specific details.

In one embodiment, the receiving entity 804B may include a diagnostic medical ultrasound system which is capable of receiving, interpreting and/or implementing the workflow 802 indicated by the set 822.

The first entity 804A may further develop a second set 826, i.e. a diagnostigraph sentence, of ideograms 812 which may represent the same workflow 802 or portion thereof as set 822 or a different portion, and communicate that set 826 to another entity 840C over a different medium of communication 830B. Where the set 826 represents the same workflow 802 or portion thereof as set 822, the set 826 may use different ideograms 812 appropriately selected to the competency level of the receiving entity 804D where that entity 804D has a difference competency level than receiving entity 804B of the set 822.

As shown in the Figure, the first entity 804A may generate a set 832, i.e. a diagnostigraph sentence, of ideograms 812 for communication 830C to themselves, such as for use in capturing notes, archiving or storing a representation of the workflow.

It will further be appreciation that the media of communications 830A, 830B, 830C is depicted as bi-directional to show that the entity 804A may be the receiver of the one or more of the sets 822 826 832, i.e. diagnostigraph sentences, with which the may then use the system 808 to interpret the diagnostigraph sentences 822, 826 or 832 and perform the workflow 802.

Figure 10G:
FIGS. 10A-10W depicts an exemplary library of diagnostigrams.
Figure 10U:

FIGS. 10A-10W depict an exemplary library 810 of diagnostigrams for use in forming diagnostigraph sentences indicating a workflow or portion thereof. In the figures, the column labeled "ID" is an identifier field which ascribes a unique identification number to each diagnostigram. It will be appreciated that there may be many methods of ascribing unique identifiers to diagnostigrams, including alphanumeric, bar code, etc. The column labeled "Type" includes keywords to aid in grouping and searching for related diagnostigrams. The column labeled "Diagnostigram" contains the pictorial or graphic representation, designed to promote ready recognition of the diagnostigram's meaning and as such indicates a diagnostigram workflow element as would be displayed on a computer screen or appear in prepared printed material. The column labeled "Glyph" contains an abstracted representation of the particular diagnostigram for use in handwritten "Stickman" notation of a particular workflow element. The column labeled "Description" contains a description of the primary meaning of the particular diagnostigram and gives usage examples. The column labeled "Literal Phoneme" contains a word or phrase which represents the particular diagnostigram in a particular entity's language and may be considered a translation of the diagnostigram's meaning into words which the user may easily understand. The column labeled "Ideographic Phoneme" contains a description of the sound(s) associated with the particular diagnostigram's meanings and is intended as a phonetic abstraction of the diagnostigram in much the same way as the glyph is a visual abstraction of the diagnostigram. It will be appreciated that fewer or more diagnostigrams may be provided in the library 810 and that the contents of the library 810 is largely implementation and application dependent such as where conforming to agreed-to standards or conventions that span application and entity groups.

Figure 11A:
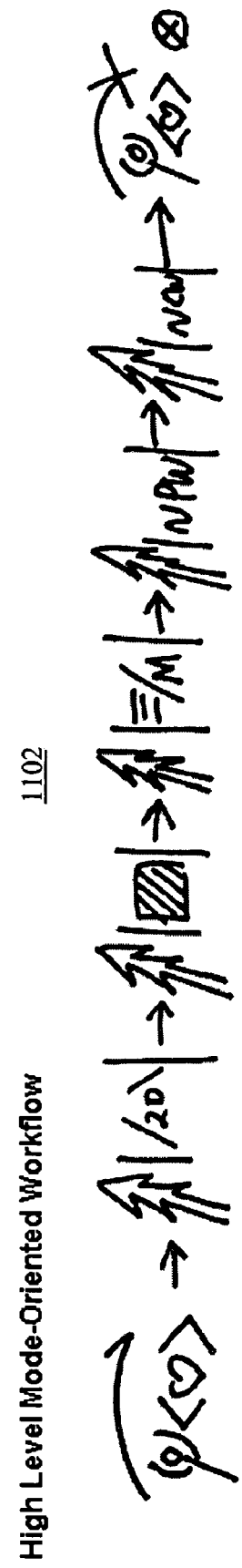

FIGS. 11A-11F depicts exemplary diagnostigraph sentences 1102 1104 1106 1108 1110 1112 1114 according to one embodiment. The diagnostigrams used in these exemplary sentences 1102 1104 1106 1108 1110 1112 1114 may all be found in the library 810 of FIGS. 10A-10W. FIG. 11A shows an exemplary diagnostigraph sentence 1102 of a high level mode oriented workflow. The sentence 1102 is an example of a diagnostigraph used for communication between expert users to indicate the modal acquisition steps of a general Cardiac study. Intermediate and lower level steps and objectives are implied. The literal phonetic version of the sentence reads: Perform Cardiac Study Setup, Optimize and analyze views and protocols in 2D, Optimize and analyze views and protocols in Color Doppler Mode, Optimize and analyze views and protocols in Motion Mode, Optimize and analyze views and protocols in Pulse Wave Doppler Mode, Optimize and analyze views and protocols in Continuous Wave Doppler Mode, End Cardiac Study, End of Workflow. The ideographic phonetic version of the sentence reads: Perf card, opt too dee, opt cee dee, opt em, opt pee wee, opt see wee, perf card stop.

Figure 11B:
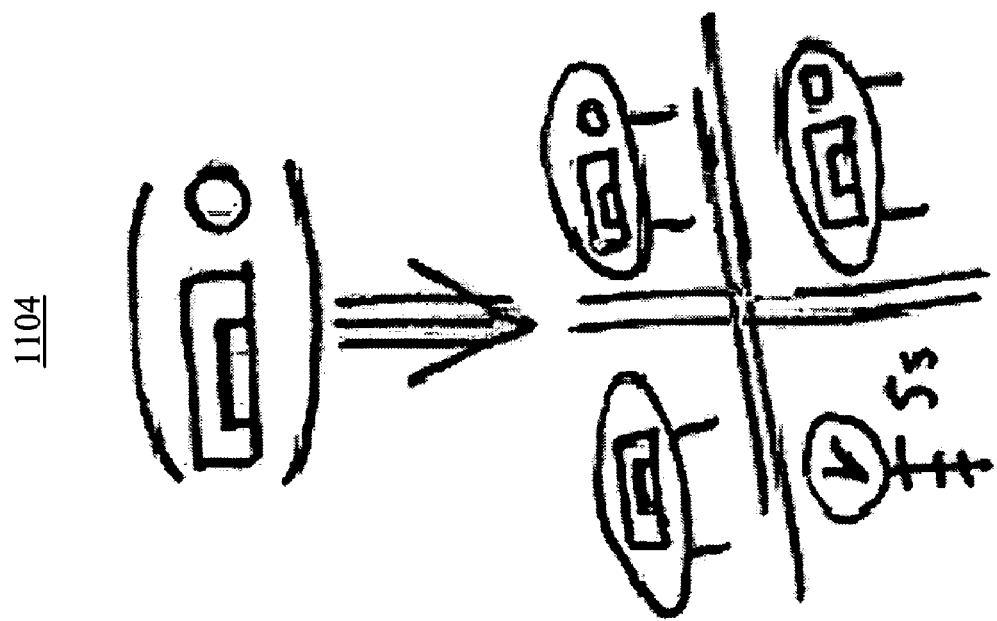

FIG. 11B shows an exemplary diagnostigraph sentence 1104 of a workflow for recording with a video recorder. This is an example of the use of an elaboration indicator and an implementation grid. The diagnostigraph sentence 1104 includes a high-level diagnostigram representative of a workflow element ("record video") and an indicator to a second level diagnostigraph sentence, including the detailed workflow elements which make up the high-level workflow element, which reads: Press VCR button, Press Record Button, Wait 5 seconds, Press VCR stop button.

FIG. 11C shows an exemplary hierarchy of diagnostigraph sentences 1106 of an intermediate level workflow. The diagnostigraph sentences 1106 are an example of the glyph notation that might be used by an experienced or lead sonographer to describe the details of "Perform Cardiac Study" in the sentence 1102 of FIG. 11A, "High Level Mode Oriented Workflow," to a less experienced sonographer. The first level, i.e. highest level diagnostigraph sentence 1108, in the depicted hierarchy 1106 of diagnostigraph sentences describes that a cardiac study will be performed. The next level down, i.e. next diagnostigraph sentence 1110 in the hierarchy 1106, describes that this is specifically an ultrasound cardiac study (Stress Echo Study), i.e. the intermediate workflow intended by "Perform Cardiac Study". The literal phonetic version of the lowest level diagnostigraph sentence 1112 reads: Enter Demographic Data, Check Cardiac Indicators to determine course of action, (Rule Out Left Ventricular Dysfunction (this case not selected)), (Rule Out Coronary Artery Disease (this case selected based on Status Frame)), Check Body Mass, (Male: Over six foot and over 250 pounds (this case not selected—transducer and workflow not shown for this case)), (Female: less than five foot and less than 100 pounds (this case not selected—workflow not shown for this case)), (other case (this case selected based on demographic data)), use 4V1 transducer, continue on next line, continued from previous line, Optimize and Analyze 2D image. "Optimize and Analyze 2D Image" comprises: Enter 2D Mode, Turn On Tissue Equalization, Perform Protocols (PLAX, PSAX, ALA, A4CH, doing 2D optimizations on each. 2D Optimizations comprises: Repeat Operations (penetration, detail and NTHI) for Apex, Mitral Valve, Aorta and Pulmonary Valve) and "Do 2D documentation" on each step. Do 2D documentation comprises: Repetition of the Operations (Capture Static Image, Capture Image Clip, Capture Cine, Record to VCR, Print Black and White Image, Print Color Image). When all repeated steps are completed, Exit 2D.

Figure 11D:
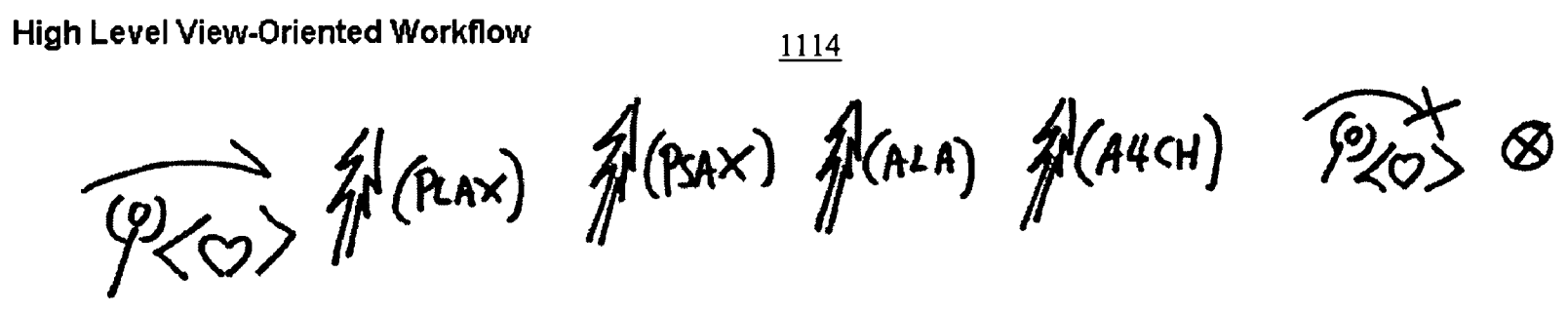

FIG. 11D shows an exemplary diagnostigraph sentence 1114 of a High Level View Oriented Workflow as an alternative to the "High Level Mode-Oriented Workflow" depicted in FIG. 11A. The sentence 1114 directs the sonographer performs optimization and analysis for each of the standard protocol views and iterates through the modes within each view. It should be noted that while this is a substantially different workflow, many of the components of the Mode-oriented workflow might be directly reused in more detailed representations of this sentence.

FIG. 11E shows an exemplary diagnostigraph sentence 1116 of a simplified contrast study procedure. The literal phonetic version of the sentence 1116 reads: Turn on the system, Use 4V1 transducer, Setup for Abdominal Study, Enter Demographic Data, Enter 2D mode, Set Depth less than 70 mm, Set Power less than 2 dB, Turn On Tissue Equalization, Set Gain to +2, View Liver, View Target State, Do 2D documentation, continue on next line (refer to FIG. 11F).

FIG. 11F shows an exemplary diagnostigraph sentence 1118 of the second portion of the diagnostigraph sentence 1116 from FIG. 11E. The literal phonetic version of the sentence 1118 reads: continued from previous line, Mandatory Activity Check for Contrast Agent, Contrast Agent Verified, Set Timer duration to 55 seconds, Inject Contrast Agent, View Contrast Image, Freeze, Previous Timer duration elapsed, Unfreeze, Set MultiHz, Scan Liver, Turn On ADI, Do 2D documentation, stop.

Diagnostigraphs are designed specifically to improve the process of creating and communicating workflow steps. The diagnostigraph framework provides a system-independent set of ideograms and syntax that is not dependent upon any specific natural language representation. Using the verification method described above, initial implementations can be deployed with confidence on specific systems. The primary benefit is reducing ambiguity and confusion in the definition and carrying out of workflow steps and thus improving quality of the exam while saving time for the designer and user.

As the scale of the Diagnostigraph library and system development expands the advantages grow. Cost savings related to the lack of dependence upon a specific natural language representation by itself seems to promise a strong return on investment for Diagnostigraphs deployed on systems sold internationally. Diagnostigram hierarchies provide built-in structural support for information detail display and hiding (ideographic zoom-in and zoom-out, along the orthogonal, structural dimension of the diagnostigraph sentence) makes the language attractive for training and documentation as well for the implementation of an on-screen workflow aid. Linkage of a well-developed library of Diagnostigraphs across several families of systems could contribute to the solution of more complex issues of workflow management as well as other related areas (system design, system maintenance).

In an alternative embodiment, translation filters linked to the meaning of a diagnostigram enable entry of workflow into a system using diagnostigrams. Input of diagnostigram-based workflows may include keystroke patterns, command streams, XML structured definitions, disambiguated phonetic mappings for voice recognition, or phoneme assisted transcription of workflow as keyed data entry, using a kind of graphical auto-completion (see next paragraph).

This process is similar to the method by which a person enters Japanese characters on a modern word processor (MS Word or Kanji Talk), starting by typing in phonemes (hiragana) with the system suggesting potential ideograms (kanji), based on the current string of phonemes, that can be inserted into the sentence at the user's selection. For instance as the user type "p-a-t", the system could display a pop-up suggesting an array of patient-related diagnostigrams accompanied by their phoneme. The user can then select the necessary diagnostigram, for example the patient registration ("PatReg") diagnostigram by completing the typed phoneme or selecting from the menu. In similar manner, a system may implemented to provide audio feedback and allow a user to speak in "Ideographic Phonemes", described above, and have suggested language specific translations ("Literal Phonemes") echoed as confirmation or to enable the user to more accurately specify a workflow element.

In another alternative embodiment, the Diagnostigraph framework may also include a set of shorthand symbols to enable clinicians, medical system designers or test engineers to quickly sketch new or capture existing workflows using pencil and paper, referred to as Stick-man Diagnostigram notation.

In another alternative embodiment, another simple input mechanism may be used for creating professional workflow documentation based on the Diagnostigram framework is a simple stencil, implemented in Microsoft Visio, manufactured by Microsoft Corp, located in Redmond, Wash., with graphics objects to represent transformation frames, screen frames, Diagnostigrams, (rendered and object outlines and suitably defined connection points). These would only be ideograms to the degree that the creators and viewers of these renderings have a common understanding of their meaning. Other more sophisticated graphics libraries might be developed in which the graphics meanings, relation, phonemes etc., may be easily manipulated by the designer/user.

The storage and representation of Diagnostigram sentences in databases and manipulated by software applications suggests the possibility of integration with workflow management systems such as Soarian, manufactured by Siemens Medical Solutions, located in Issaquah, Wash.

In application of the above described embodiments, clinical experts and engineers would work together using Diagnostigraphs to capture a wide array of existing workflows as well as designing new workflows. Incorporated into a system with professionally developed graphics and a tested library of elements, Diagnostigraph based software and documentation may replace ad-hoc scenario descriptions in new systems, in Ultrasound development facilities, clinics and possibly throughout the medical industry.

A Diagnostigraph sentence is ideally suited to presentation as an on-screen widget for displaying workflow steps and current status within the workflow. Such a widget might be sized and displayed in such a way that it can be incorporated into the flow of operations the user must perform. The Diagnostigraph Widget may be collapsed into a postage stamp display or expanded into a cinematic display of frames that represent the instruction steps. In a design environment, these steps may be expanded to the implementation layer for "white box" verification of the actual functions executed by the receiving entity. The Diagnostigrams within these frames are pictures always bound with their meaning and relationships and thus drill-down or mouse-over popup capabilities, similar to Intellisense® technology developed by Microsoft Corporation, located in Redmond, Wash., for instant help may be available to avoid fumbling through a multi-step help search. In addition these meanings and relations might be further linked to operations, providing a semantically meaningful way for the user to perform or verify portions of the workflow and thus provide a consistent way to deliver automation of complex workflows or procedures.

As the Diagnostigraph framework and associated libraries are optimized and incorporate a wide set of real world data it could then be deployed as a standard and Diagnostigraphs could provide a way for workflow management systems to automate the communication of resultant scenarios to the varied roles within the workflow path with the potential for the framework, the library content and/or Diagnostigraph-based software components to be licensed to other Medical Device companies and other providers within the Healthcare Enterprise.

To clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superceding any other implied definitions herebefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

It is therefore intended that the foregoing detailed description be regarded as illustrative rather than limiting, and that it be understood that it is the following claims, including all equivalents, that are intended to define the spirit and scope of this invention.

I claim:

1. A system for communicating a workflow between at least two entities, the workflow comprising one or more of a plurality of workflow elements, the system comprising:
   a plurality of ideograms, each of the plurality of ideograms comprising a visual indication of at least one workflow element of the plurality of workflow elements and capable of conveying a connotation of the at least one workflow element to the at least two entities not dependent upon any specific natural language representation of the at least one workflow element;
   a syntax defining interpretation of each of the plurality of ideograms alone and in combination with at least another of the plurality of ideograms, the syntax operative to allow selection and relation of a subset of the plurality of ideograms by one of the at least two entities to represent at least a portion of the workflow to another of the at least two entities and;
   a diagnostic medical imaging system associated with at least one of the at least two entities and responsive to execution of those workflow elements indicated by the subset of the plurality of ideograms to implement the portion of the workflow represented thereby relevant to the operation of the diagnostic medical imaging system.

2. The system of claim 1, wherein at least one of the at least two entities comprises at least one of a user of the workflow, a participant in the workflow, a creator of the workflow, an instructor of the workflow, a computer, a graphic user interface, a sonographer, a radiologist, a clinician, a diagnostic medial ultrasound system, a medical review station, a hand-held computer, a cellular telephone, a personal computer, a diagnostic medical ultrasound image acquisition software program, a diagnostic software computer program, a database, a medical examination computer program, a medical study review computer program, or combinations thereof.

3. The system of claim 1, wherein each of the plurality of workflow elements comprises at least one of an act, an objective, an event, a relationship between an act, event or objective, or combinations thereof.

4. The system of claim 1, wherein the plurality of ideograms further comprises:
   at least one action ideogram comprising a visual indication of at least one of a plurality of acts to be performed by at least one of the at least two entities; and
   at least one objective ideogram comprising a visual indication of at least one of a plurality of objectives.

5. The system of claim 4, wherein each of the plurality of objectives comprises at least one goal related to the performance of at least one of the plurality of acts.

6. The system of claim 5, wherein the goal is to be avoided.

7. The system of claim 5, wherein the goal comprises at least one expected result of the performance of the at least one of the plurality of acts.

8. The system of claim 5, wherein the workflow comprises a diagnostic medical ultrasound workflow and one of the at least two entities comprises a diagnostic medical ultrasound system, the goal comprises a state of the diagnostic medical ultrasound system.

9. The system of claim 4, wherein at least one objective ideogram is preceded by at least one action ideogram in the representation of the workflow, the at least one objective ideogram further comprising a visual representation of a state achieved via execution of all of the plurality of acts represented by the at least one action ideogram.

10. The system of claim 4, wherein the at least one objective ideogram comprises a visual representation of a visual appearance of the at least one of the plurality of objectives.

11. The system of claim 10, wherein the at least one objective ideogram comprises a visual representation of a computer screen display.

12. The system of claim 4, wherein the plurality of acts comprises an act of verifying a condition.

13. The system of claim 12, wherein the act of verifying a condition further comprises verifying that the condition has occurred.

14. The system of claim 13, wherein the syntax further defines that wherein the at least one action ideogram which represents the act of verifying a condition precedes another of the at least one action ideogram, performance of the act visually indicated by the subsequent at least one action ideogram is dependent upon the verification of the condition.

15. The system of claim 12, wherein the act of verifying a condition further comprises waiting for the condition to occur.

16. The system of claim 12, wherein the plurality of acts further comprises an act of alerting when the condition is verified.

17. The system of claim 12, wherein the syntax further defines the act of verifying a condition to be one of waiting for the condition to occur or verifying that the condition has occurred based on a combination of the action ideogram representative of the act of verifying a condition in relation to another of the plurality of ideograms.

18. The system of claim 4, wherein the plurality of acts comprises inaction.

19. The system of claim 1, wherein the plurality of ideograms further comprises at least one event ideogram comprising a visual indication of an expected event caused by an entity other than the at least two entities.

20. The system of claim 1, wherein the plurality of ideograms further comprises at least one relationship ideogram comprising a visual indication of a relationship between at least two of the plurality of ideograms.

21. The system of claim 20, wherein the at least one relationship ideogram comprises a visual indication of an ordering between the at least two of the plurality of ideograms.

22. The system of claim 21, wherein the ordering may be at least one of sequential, linear, discontinuous, circular, parallel, structural, hierarchical, temporal or combinations thereof.

23. The system of claim 1, wherein each of the plurality of ideograms further comprises at least one constituent ideogram.

24. The system of claim 23, wherein the at least one constituent ideogram is representative of an element of a diagnostic medical imaging workflow.

25. The system of claim 1, wherein an interpretation of each ideogram of the plurality of ideograms may be altered by the context in which the ideogram is utilized.

26. The system of claim 1, wherein the syntax further defines that each of the plurality of ideograms may comprise a first interpretation when utilized alone and a second interpretation when utilized in combination with at least one other of the plurality of ideograms.

27. The system of claim 26, wherein the second interpretation may be more specific than the first interpretation.

28. The system of claim 26, wherein the second interpretation may be broader than the first interpretation.

29. The system of claim 26, wherein the second interpretation may be the opposite of the first interpretation.

30. The system of claim 1, wherein each of the plurality of ideograms comprises an unambiguous interpretation by at least both of the at least two entities.

31. The system of claim 1, wherein each of the plurality of ideograms comprises a first verbalization when used alone and a second verbalization when used in combination with another of the plurality of ideograms.

32. The system of claim 1, wherein the interpretation of one of the plurality of ideograms may be indicated by a combination of at least two other of the plurality of ideograms.

33. The system of claim 32, wherein the one of the plurality of ideograms further visually refers to the combination of at least two other of the plurality of ideograms.

34. The system of claim 1, wherein the representation of the workflow directs performance of the workflow without disrupting the performance.

35. The system of claim 1, wherein the workflow comprises a diagnostic medical ultrasound workflow.

36. The system of claim 35, wherein the diagnostic medical ultrasound workflow comprises a medical ultrasound examination.

37. The system of claim 1, wherein one of the entities comprises a diagnostic medical ultrasound machine, the representation of the workflow being capable of being input and interpreted by the diagnostic medical ultrasound machine.

38. The system of claim 1, wherein one of the entities comprises a diagnostic medical ultrasound machine, the representation of the workflow being capable of being generated by the diagnostic medical ultrasound machine.

39. The system of claim 38, wherein the diagnostic medical ultrasound machine is further capable of generating the representation of the workflow in response to activity by a user of the diagnostic medical ultrasound machine.

40. The system of claim 1, wherein one of the entities comprises a diagnostic medical ultrasound machine, the representation of the workflow being representative of a log of a user's interactions with the diagnostic medical ultrasound machine.

41. A method of communicating a workflow between at least two entities, the workflow comprising one or more of a plurality of workflow elements, the method comprising:
    providing a plurality of ideograms, each of the plurality of ideograms comprising a visual indication of at least one workflow element of the plurality of workflow elements and capable of conveying a connotation of the at least one workflow element to the at least two entities not dependent upon any specific natural language representation of the at least one workflow element;
    providing a syntax defining interpretation of each of the plurality of ideograms alone and in combination with at least another of the plurality of ideograms, the syntax operative to allow selection and relation of a subset of the plurality of ideograms by one of the at least two entities to represent at least a portion of the workflow to another of the at least two entities;
    allowing at least one of the at least two entities to select and relate a subset of the plurality of ideograms to represent at least a portion of the workflow for communication between the at least two entities; and
    operating a diagnostic medical imaging system by at least one of the at least two entities responsively to those workflow elements indicated by the subset of the plurality of ideograms to implement the portion of the workflow represented thereby relevant to the operation of the diagnostic medical imaging system.

42. The method of claim 41, wherein at least one of the at least two entities comprises at least one of a user of the workflow, a participant in the workflow, a creator of the workflow, an instructor of the workflow, a computer, a graphic user interface, a sonographer, a radiologist, a clinician, a diagnostic medial ultrasound system, a medical review station, a handheld computer, a cellular telephone, a personal computer, a diagnostic medical ultrasound image acquisition software program, a diagnostic software computer program, a database, a medical examination computer program, a medical study review computer program, or combinations thereof.

43. The method of claim 41, wherein each of the plurality of workflow elements comprises at least one of an act, an objective, an event, a relationship between an act, event or objective, or combinations thereof.

44. The method of claim 41, wherein the plurality of ideograms further comprises at least one event ideogram comprising a visual indication of an expected event caused by an entity other than the at least two entities.

45. The method of claim 41, wherein the plurality of ideograms further comprises:
    at least one action ideogram comprising a visual indication of at least one of a plurality of acts to be performed by at least one of the at least two entities; and
    at least one objective ideogram comprising a visual indication of at least one of a plurality of objectives.

46. The method of claim 45, wherein at least one objective ideogram is preceded by at least one action ideogram in the representation of the workflow, the at least one objective ideogram further comprising a visual representation of a state achieved via execution of all of the plurality of acts represented by the at least one action ideogram.

47. The method of claim 45, wherein the at least one objective ideogram comprises a visual representation of a visual appearance of the at least one of the plurality of objectives.

48. The method of claim 45, wherein the plurality of acts comprises an act of verifying a condition.

49. The method of claim 45, wherein the plurality of acts comprises inaction.

50. The method of claim 41, wherein the plurality of ideograms further comprises at least one relationship ideogram comprising a visual indication of a relationship between at least two of the plurality of ideograms.

51. The method of claim 50, wherein the at least one relationship ideogram comprises a visual indication of an ordering between the at least two of the plurality of ideograms.

52. The method of claim 51, wherein the ordering may be at least one of sequential, linear, discontinuous, circular, parallel, hierarchical, temporal or combinations thereof.

53. The method of claim 41, wherein the selection and relation alters an interpretation of at least one ideogram of the subset of the plurality of ideograms based on the context in which the at least one ideogram is utilized.

54. The method of claim 41, wherein the syntax further defines that each of the plurality of ideograms may comprise a first interpretation when utilized alone and a second interpretation when utilized in combination with at least one other of the plurality of ideograms.

55. The method of claim 54, wherein the second interpretation may be more specific than the first interpretation.

56. The method of claim 54, wherein the second interpretation may be broader than the first interpretation.

57. The method of claim 54, wherein the second interpretation may be the opposite of the first interpretation.

58. The method of claim 41, wherein each of the plurality of ideograms comprises an unambiguous interpretation by at least both of the at least two entities.

59. The method of claim 41, wherein each of the plurality of ideograms comprises a first verbalization when used alone and a second verbalization when used in combination with another of the plurality of ideograms.

60. The method of claim 41, wherein the interpretation of one of the plurality of ideograms may be indicated by a combination of at least two other of the plurality of ideograms.

61. The method of claim 60, wherein the one of the plurality of ideograms further visually refers to the combination of at least two other of the plurality of ideograms.

62. The method of claim 41, wherein the representation of the workflow directs performance of the workflow without disrupting the performance.

63. The method of claim 41, wherein the workflow comprises a diagnostic medical ultrasound workflow.

64. The method of claim 63, wherein the diagnostic medical ultrasound workflow comprises a medical ultrasound examination.

65. The method of claim 41, wherein one of the entities comprises a diagnostic medical ultrasound machine, the representation of the workflow being capable of being input and interpreted by the diagnostic medical ultrasound machine.

66. The method of claim 41, wherein one of the entities comprises a diagnostic medical ultrasound machine, the allowing further comprising selection and relation, by the diagnostic medical ultrasound machine, to represent the workflow.

67. The method of claim 66, wherein the diagnostic medical ultrasound machine is further capable of generating the representation of the workflow in response to activity by a user of the diagnostic medical ultrasound machine.

68. The method of claim 41, wherein one of the entities comprises a diagnostic medical ultrasound machine, the representation of the workflow being representative of a log of a user's interactions with the diagnostic medical ultrasound machine.

69. A system for communicating a workflow between at least two entities, the workflow comprising one or more of a plurality of workflow elements, the system comprising:
   a plurality of ideogram means for visually indicating at least one workflow element of the plurality of workflow elements and capable of conveying a connotation of the at least one workflow element to the at least two entities not dependent upon any specific natural language representation of the at least one workflow element;
   a syntax means for defining interpretation of each of the plurality of ideogram means alone and in combination with at least another of the plurality of ideogram means, the syntax operative to allow selection and relation of a subset of the plurality of ideogram means by one of the at least two entities to represent at least a portion of the workflow to another of the at least two entities; and
   a diagnostic medical imaging means associated with at least one of the at least two entities and responsive to execution of those workflow elements indicated by the subset of the plurality of ideograms to implement the portion of the workflow represented thereby relevant to the operation of the diagnostic medical imaging system.

70. A system for communicating a diagnostic medical ultrasound workflow between at least two entities, the diagnostic medical ultrasound workflow comprising one or more of a plurality of workflow elements associated with the operation of a diagnostic medical ultrasound system, the system comprising:
   a plurality of ideograms, each of the plurality of ideograms comprising a visual indication of at least one workflow element of the plurality of diagnostic medical ultrasound workflow elements and capable of conveying a connotation of the at least one workflow element to the at least two entities not dependent upon any specific natural language verbalization of the at least one workflow element; and
   a syntax defining interpretation of each of the plurality of ideograms alone and in combination with at least another of the plurality of ideograms, the syntax operative to allow selection and relation of a subset of the plurality of ideograms by one of the at least two entities to represent at least a portion of the diagnostic medical ultrasound workflow to another of the at least two entities; and
   wherein the diagnostic medical imaging system is associated with at least one of the at least two entities and responsive to execution of those workflow elements indicated by the subset of the plurality of ideograms to implement the portion of the workflow represented thereby relevant to the operation of the diagnostic medical imaging system.

* * * * *